(12) United States Patent
Tomiuk

(10) Patent No.: US 10,337,042 B2
(45) Date of Patent: Jul. 2, 2019

(54) METHOD FOR PRODUCING GALACTOOLIGOSACCHARIDES FROM LACTOSE

(71) Applicant: VITALUS NUTRITION INC., Abbotsford (CA)

(72) Inventor: Stephen Tomiuk, Abbotsford (CA)

(73) Assignee: Vitalus Nutrition Inc., Abbotsford, BC (CA)

( * ) Notice: Subject to any disclaimer, the term of this patent is extended or adjusted under 35 U.S.C. 154(b) by 0 days.

(21) Appl. No.: 15/923,957

(22) Filed: Mar. 16, 2018

(65) Prior Publication Data

US 2018/0201965 A1 Jul. 19, 2018

Related U.S. Application Data

(63) Continuation-in-part of application No. PCT/CA2017/050042, filed on Jan. 12, 2017, and a continuation-in-part of application No. PCT/CA2017/051598, filed on Dec. 22, 2017.

(60) Provisional application No. 62/277,838, filed on Jan. 12, 2016.

(51) Int. Cl.

| | | |
|---|---|---|
| *C12P 19/14* | (2006.01) | |
| *C07H 3/06* | (2006.01) | |
| *A23K 20/163* | (2016.01) | |
| *C12P 19/02* | (2006.01) | |
| *A23L 33/24* | (2016.01) | |
| *A23L 33/21* | (2016.01) | |

(52) U.S. Cl.
CPC ............ *C12P 19/14* (2013.01); *A23K 20/163* (2016.05); *A23L 33/21* (2016.08); *A23L 33/24* (2016.08); *C07H 3/06* (2013.01); *C12P 19/02* (2013.01); *A23V 2002/00* (2013.01)

(58) Field of Classification Search
CPC ....... C12P 19/14; C12P 19/02; A23V 2002/00
See application file for complete search history.

(56) References Cited

U.S. PATENT DOCUMENTS

2010/0254949 A1 10/2010 Barboza et al.

FOREIGN PATENT DOCUMENTS

| CN | 104975056 A | 10/2015 |
| CN | 105274164 A | 1/2016 |
| CN | 105274165 A | 1/2016 |
| WO | 2010/105207 A1 | 9/2010 |
| WO | 2015/012597 A1 | 1/2015 |

OTHER PUBLICATIONS

Urrutia (Journal of Agricultural and Food Chemistry; 2013, 61, 1081-1087).*

International Search Report, dated Apr. 25, 2017, for corresponding International Application PCT/CA2017/050042, filed Jan. 12, 2017, 3 pages.
Written Opinion, dated Apr. 25, 2017, for corresponding International Application PCT/CA2017/050042, dated Jan. 12, 2017, 5 pages.
Adamczak, M. et al, "*Influence of reaction medium composition on enzymatic synthesis of galactooligosaccharides and lactulose from lactose concentrates prepared from whey permeate*". Chemical Papers, Apr. 2009 (Apr. 2009), vol. 63(2), pp. 111-116.
Guerrero, C. et al, "*Transgalactosylation and hydrolytic activities of commercial preparations of β-galactosidase for the synthesis of prebiotic carbohydrates*". Enzyme and Microbial Technology, Mar. 2015 (Mar. 2015), vol. 70, pp. 9-17.
Chen, Xiao Yan et al., "Lactose and lactose-derived oligosaccharides: More than prebiotics?," International Dairy Journal 67 (2017), pp. 61-72, Elsevier B.V., The Netherlands.
Urrutia, Paulina et al., "Detailed Analysis of Galactooligosaccharides Synthesis with β-Galactosidase from *Aspergillus oryzae*," Journal of Agricultural and Food Chemistry, Jan. 2013, 61 (5), pp. 1081-1087, ACS Publications, Washington, DC.
Van Leeuwen, Sander S. et al., "Comparative structural characterization of 7 commercial galacto-oligosaccharide (GOS) products," Carbohydrate Research 425 (2016), pp. 48-58, Elsevier B.V., The Netherlands.
Van Leeuwen, Sander S. et al., "Development of a $^1$H NMR structural-reporter-group concept of the analysis of prebiotic galacto-oligosaccharides of the [β- D -Galp-(1→χ]$_n$-D-Glcp type," Carbohydrate Research, 400 (2014), pp. 54-58, http://dx.doi.org/10.1016/j.carres.2014.08.011, Elsevier B.V., The Netherlands.
Van Leeuwen, Sander S. et al., "'$^1$H NMR analysis of the lactose/ β-galactosidase-derived galacto-oligosaccharide components of Vivinal® GOS up to DP5," Carbohydrate Research 400 (2014), pp. 59-73, Elsevier B.V., The Netherlands.
Supplementary European Search Report, dated Sep. 17, 2018, for European application, EP2017738066, 11 pages.
Park, Ah-Reum et al., "Galacto-Oligosaccharaide Production Using Microbial β-Galactosidase: Current State and Perspectives", Applied Microbiology and Biotechnology, vol. 85, No. 5, Nov. 27, 2009, pp. 1279-1286.
Vera, Carlos et al., "Synthesis of Galacto-Oligosaccharides by β-galactosidase from *Aspergillus Oryzae* Using Partially dissolved and Supersaturated Solution of Lactose," Enzyme and Microbial Technology, vol. 50, Mar. 10, 2012, pp. 188-194.
International Search Report, dated Sep. 5, 2018, for corresponding International Application PCT/CA2017/051598, filed Dec. 22, 2017, 3 pages.
Written Opinion, dated Sep. 5, 2018, for corresponding International Application PCT/CA2017/051598, dated Dec. 22, 2017, 5 pages.

* cited by examiner

*Primary Examiner* — Pancham Bakshi
(74) *Attorney, Agent, or Firm* — Kilpatrick Townsend & Stockton LLP

(57) ABSTRACT

Methods are disclosed for the enzymatic preparation of galactooligosaccharide (GOS) from lactose using two different microbial lactase enzymes to maximize the extent of transgalactosylation during the digestion of lactose. Methods are also disclosed for avoiding the turbidity of a solution comprising GOS and lactose as it is adjusted for incubation with a yeast neutral lactase.

30 Claims, 9 Drawing Sheets

METHOD FOR PRODUCING GALACTOOLIGOSACCHARIDES FROM LACTOSE

CROSS-REFERENCE TO RELATED APPLICATIONS

This application is a continuation-in-part (CIP) of International Patent Application No. PCT/CA2017/051598 filed Dec. 22, 2017, which is hereby incorporated by reference in its entirety. This application is also a CIP of International Patent Application No. PCT/CA2017/050042 filed Jan. 12, 2017, which claims priority from U.S. Provisional Application No. 62/277,838 filed Jan. 12, 2016, each of which is hereby incorporated by reference in its entirety.

BACKGROUND

1. Field

This disclosure relates to the enzymatic preparation of galactooligosaccharide (GOS) from lactose. More particularly, this disclosure relates to the sequential use of two different microbial lactase enzymes to maximize the degree of transgalactosylation during the digestion of lactose.

2. Description of Related Art

Galactooligosaccharides (GOS) are non-digestible carbohydrates that serve as the building block of oligosaccharides in human milk. GOS modulate the growth and activity of gastrointestinal microorganisms, and are therefore believed to promote a healthy balance of microorganisms in the gut. Among other things, GOS are believed to reduce levels of blood serum cholesterol, improve mineral absorption, and prevent colon cancer development. The properties of GOS depend significantly on the chemical composition, structure, and degree of polymerization (DP).

GOS can be formed by the digestion of lactose with β-D-galactoside galactohydrolases. β-D-galactoside galactohydrolases catalyze the hydrolysis of the galactosyl moiety from the non-reducing end of lactose. In addition, β-D-galactoside galactohydrolases can catalyze transgalactosylation in which a galactosyl moiety is transferred to a nucleophilic acceptor other than water, i.e. potentially any sugar present in a reaction medium. Transgalactosylation is a kinetically controlled reaction, and represents competition between the reactions of hydrolysis and synthesis. The ability to favor synthesis over hydrolysis depends on several factors, including the origin of the β-D-galactoside galactohydrolase and the initial composition of acceptor sugars in the medium (e.g. lactose and galactose) with which the enzymes are presented. If lactose is the initial substrate, transgalactosylation results in the production of GOS comprising a mixture of di-(DP2), tri-(DP3), and even higher oligosaccharides (DP4+) with or without a terminal glucose. The chemical structure and composition of a GOS (e.g. the number of hexose moieties and the types of linkages) affects its properties, such as the fermentation pattern by probiotic bacteria in the gut. The chemical compositions, structure, degree of polymerization, and yield of GOS also depends on the origin of the β-D-galactoside galactohydrolases utilized.

Many adults are lactose intolerant, and thus it is desirable to hydrolyze as much lactose as possible during the preparation of GOS from lactose. However, reaction conditions that favor the enzymatic digestion of lactose to, for example, less than 20% of the initial lactose concentration tend to also favor the digestion of GOS that is synthesized. Accordingly, reducing lactose concentration may result in reduced yield of GOS.

SUMMARY

This disclosure relates to a method of producing galactooligosaccharide (GOS) from lactose. The method includes incubating an initial aqueous solution comprising lactose at an initial concentration with an acid fungal lactase to produce an intermediate aqueous solution comprising lactose and GOS in which the concentration of lactose is about 30% to about 70% of the initial concentration of the initial aqueous solution; adding a yeast lactase to the intermediate aqueous solution; and incubating the intermediate aqueous solution comprising the yeast lactase to produce a final aqueous solution in which the concentration of lactose is between 0% and 20% of the initial concentration of the initial aqueous solution. Incubating the initial aqueous solution to produce the intermediate aqueous may involve incubating the initial aqueous solution to produce the intermediate aqueous having about 40% of the initial concentration of lactose the initial aqueous solution. Incubating the initial aqueous solution to produce the intermediate aqueous may involve incubating the initial aqueous solution to produce the intermediate aqueous comprising 49% to 52% DP2 sugar (w/w) of total sugar in the intermediate aqueous solution. Incubating the intermediate aqueous solution with the yeast lactase to produce the final aqueous solution, may involve incubating the intermediate aqueous solution to produce the final aqueous solution comprising 23.5% to 25% DP2 sugar (w/w) of total sugar in the final aqueous solution.

The method may further include adjusting the pH of the intermediate aqueous solution to between 5.5 and 9.0 with KOH, $MgCl_2$, and citric acid prior to adding the yeast lactase. Adjusting the pH of the intermediate aqueous solution to between 5.5 and 9.0 with KOH, $MgCl_2$, and citric acid may include adjusting the pH to between 6.0 and 7.5. Adjusting the pH of the intermediate aqueous solution to between 5.5 and 9.0 with KOH, $MgCl_2$, and citric acid may include adjusting the pH to about 6.8. Adjusting the pH of the intermediate aqueous solution with KOH, $MgCl_2$, and citric acid may include sequentially adding KOH, $MgCl_2$, and citric acid to the intermediate aqueous solution. Sequentially adding KOH, $MgCl_2$, and citric acid to the intermediate aqueous solution comprises, in sequential order: adjusting the pH of the intermediate aqueous solution to about 9.2 with KOH; adding about 0.16 g of $MgCl_2$ per 100 g of aqueous solution to the intermediate aqueous solution; and adjusting the pH of the intermediate aqueous solution from about 9.1 to about 6.8.

The acid fungal lactase may be a fungal β-D-galactoside galactohydrolase.

The fungal β-D-galactoside galactohydrolase may be derived from an *Aspergillus* species. The *Aspergillus* species may be *Aspergillus oryzae*. The concentration of the acid fungal lactase may be expressed in terms of lactase units (LU) per gram of lactose in the solution. The concentration of the acid fungal lactase in the initial aqueous solution may be between 1 and 300 LU per gram of lactose in the initial aqueous solution. The concentration of the acid fungal lactase may be between about 10 and about 20 LU per gram of lactose in the initial aqueous solution. The concentration of the acid fungal lactase may be between about 15 and about 17 LU per gram of lactose in the initial aqueous solution. The concentration of the acid fungal lactase may be about 16.7 LU per gram of lactose in the initial aqueous solution. Alternatively, the concentration of the acid fungal lactase may be about 5.6 LU per gram of lactose in the initial aqueous solution, or about 5.8 LU per gram of lactose in the initial aqueous solution.

The yeast neutral lactase may be a yeast β-D-galactoside galactohydrolase. The yeast β-D-galactoside galactohydrolase may be derived from a *Kluyveromyces* species. The *Kluyveromyces* species may be *Kluyveromyces lactis*.

Adding the yeast neutral lactase to the intermediate aqueous solution may include adding the yeast lactase to a concentration of between 1 and 50 LU per gram of lactose in the intermediate aqueous solution. Adding the yeast neutral lactase to the intermediate aqueous solution may include adding the yeast lactase to a concentration of about 4 to about 5 LU per gram of lactose in the intermediate aqueous solution. Adding the yeast neutral lactase to the intermediate aqueous solution may include adding the yeast lactase to a concentration of about 4.7 LU per gram of lactose in the intermediate aqueous solution. Adding the yeast neutral lactase to the intermediate aqueous solution may include adding the yeast lactase to a concentration of about 4.4 LU per gram of lactose in the intermediate aqueous solution.

The initial concentration of lactose in the initial aqueous solution may be between 15 and 63 ° Bx. The initial concentration of lactose in the initial aqueous solution may be between about 30° Bx and about 60 ° Bx. The initial concentration of lactose in the initial aqueous solution may be about 45 ° Bx. The initial concentration of lactose in the initial aqueous solution may be about 53 ° Bx.

The initial aqueous solution may be incubated with the fungal acid lactase at a temperature between about 25 and 65° C. The temperature may be between about 40 and about 55° C. The initial aqueous solution may be incubated with the fungal lactase at a temperature of about 53.5° C.

The initial aqueous solution may be incubated with the fungal lactase at a pH between about 2.5 and about 8.0. The initial aqueous solution may be incubated with the fungal lactase at a pH between about 3.5 and about 6.5. In particular embodiments, the initial aqueous solution is incubated with the fungal lactase at a pH between about 4.5 and about 5.5.

In some embodiments, the method includes deactivating the fungal acid lactase prior to adding the yeast neutral lactase. In some embodiments, deactivating the fungal lactase comprises adjusting the pH of the intermediate aqueous solution to about 2 or less. In some embodiments, deactivating the fungal acid lactase includes adjusting the pH of the intermediate aqueous solution to about 2. The pH of the intermediate aqueous solution may be adjusted with hydrochloric acid (HCl) to deactivate the fungal lactase. In some embodiments, deactivating the fungal acid lactase includes heating to above 72° C.

The intermediate aqueous solution may incubated with the yeast neutral lactase at a temperature between about 4 and about 50° C. In some embodiments, the intermediate aqueous solution is incubated with the yeast lactase at a temperature between about 30 and about 45° C. In some embodiments, the intermediate aqueous solution is incubated with the yeast lactase at a temperature of about 36.5° C.

The method may further include deactivating the yeast lactase. In some embodiments, deactivating the yeast lactase includes adjusting the pH of the final aqueous solution to about pH 5.5. In some embodiments, the pH of the final aqueous solution is adjusted to about pH 5.5 with citric acid. In some embodiments, deactivating the yeast lactase includes incubating the final aqueous solution at 72° C.

The method may further include partially removing glucose and galactose from the final aqueous solution by chromatography to produce a GOS-enriched solution.

The method may further include removing the fungal acid lactase, the yeast neutral lactase, glucose and galactose from the final aqueous solution by chromatography.

In some embodiments, the fungal acid lactase and the yeast neutral lactase, is removed from the final aqueous solution by ion exchange chromatography.

In some embodiments, the glucose and/or galactose is at least partially removed from the final aqueous solution by ion exchange, filtration, chromatographic separation, or additional fermentation reactions. In some embodiments, chromatographic separation comprises simulated moving bed chromatography.

This disclosure further relates to a galactooligosaccharide (GOS) syrup produced according to a method as described above. In some embodiments, the GOS syrup is at least 40% GOS w/w of the total carbohydrate in the GOS syrup. In some embodiments, the GOS syrup is at least 65% GOS w/w of the total carbohydrate in the GOS syrup.

In some embodiments, the wherein ratio of DP2:DP3:DP4 in the GOS syrup is about 2:3:1.

This disclosure also relates generally to the use of a β-D-galactoside galactohydrolase derived from *Aspergillus oryzae* in combination with a β-D-galactoside galactohydrolase derived from *Kluyveromyces lactis* in the preparation of galactooligosaccharide (GOS) syrup from an aqueous solution comprising lactose, wherein the GOS syrup is at least about 40% GOS w/w of the total carbohydrate in the GOS syrup. The β-D-galactoside galactohydrolase derived from *Aspergillus oryzae* is for incubation with the aqueous solution prior to incubation of the aqueous solution with the β-D-galactoside galactohydrolase derived from *Kluyveromyces lactis*.

In some embodiments, the GOS syrup may be at least about 60% GOS w/w of the total carbohydrate in the GOS syrup. In some embodiments, the GOS syrup may be about 65% GOS w/w of the total carbohydrate in the GOS syrup.

This disclosure also relates generally to the use of a β-D-galactoside galactohydrolase derived from *Kluyveromyces lactis* for increasing the amount of galactooligosaccharide (GOS) in an aqueous solution comprising lactose that has been previously treated with a β-D-galactoside galactohydrolase derived from *Aspergillus oryzae*. In some embodiments, the amount of GOS may be increased to at least 40% w/w of total carbohydrates in the solution. In some embodiments, the diversity of GOS may be increased.

This disclosure also relates generally to the use of a β-D-galactoside galactohydrolase derived from *Aspergillus oryzae* in combination with a β-D-galactoside galactohydrolase derived from *Kluyveromyces lactis* in reducing the concentration of lactose in an aqueous solution to less than 20% w/w of the initial concentration of lactose. The β-D-galactoside galactohydrolase derived from *Aspergillus oryzae* is for incubation with the aqueous solution prior to incubation of the aqueous solution with the β-D-galactoside galactohydrolase derived from *Kluyveromyces lactis*.

The skilled person will understand that "aqueous solutions" are an aqueous mixtures, but that aqueous mixtures may also include other water-based compositions including aqueous suspensions. In other words, the skilled person will understand that "aqueous mixture" as used herein includes aqueous solutions as well as aqueous suspensions.

Accordingly, various aspects of this disclosure more generally relate to a method of producing galactooligosaccharide (GOS) from lactose, the method comprising: incubating an initial aqueous mixture comprising lactose at an initial concentration with an acid lactase to produce an intermediate aqueous mixture comprising lactose and GOS in which the concentration of lactose is about 30% to about 70% of the initial concentration of the initial aqueous mixture; adding a neutral lactase to the intermediate aqueous mixture; and incubating the intermediate aqueous mixture comprising the neutral lactase to produce a final aqueous mixture in which the concentration of lactose is about 20% or less of the initial concentration of the initial aqueous mixture.

The acid lactase may be an acid β-D-galactoside galactohydrolase. The neutral lactase may be a neutral β-D-galactoside galactohydrolase. The acid lactase ma be an acid β-D-galactoside galactohydrolase derived from *Aspergillus oryzae*. The neutral lactase may be a neutral β-D-galactoside galactohydrolase derived from *Kluyveromyces lactis*.

The concentration of the acid lactase in the initial aqueous mixture may be: between 1 and 300 lactase units (LU) per gram of lactose in the initial aqueous mixture; about 5.6 LU per gram of lactose in the initial aqueous mixture; about 5.7 LU per gram of lactose in the initial aqueous mixture; or about 5.8 LU per gram of lactose in the initial aqueous mixture.

Adding the neutral lactase to the intermediate aqueous mixture may include adding the neutral lactase to a concentration of: between 1 and 50 lactase units (LU) per gram of lactose in the intermediate aqueous mixture; about 4.4 LU per gram of lactose in the intermediate aqueous mixture; about 4.5 LU per gram of lactose in the intermediate aqueous mixture; about 4.6 LU per gram of lactose in the intermediate aqueous mixture; or about 4.7 LU per gram of lactose in the intermediate aqueous mixture.

The method may further include adjusting the intermediate aqueous mixture prior to adding the neutral lactase, wherein adjusting the intermediate aqueous mixture comprises adjusting the pH of the intermediate aqueous mixture to between 5.5 and 9.0. Adjusting the intermediate aqueous mixture prior to adding the neutral lactase may include adjusting the intermediate mixture with KOH, $MgCl_2$, and citric acid.

Adjusting the pH of the intermediate aqueous mixture to between 5.5 and 9.0 may include sequentially adding KOH, $MgCl_2$, and citric acid to the intermediate aqueous mixture. Sequentially adding KOH, $MgCl_2$, and citric acid to the intermediate aqueous mixture may include, in sequential order: adjusting the pH of the intermediate aqueous mixture to about 9.2 with KOH; adding about 0.16 g of $MgCl_2$ per 100 g of aqueous mixture to the intermediate aqueous mixture; and adjusting the pH of the intermediate aqueous mixture to between 5.5 and 9.0 with citric acid. Adjusting the pH of the intermediate aqueous mixture to between 5.5 and 9.0 with citric acid may include adjusting the pH of the intermediate aqueous mixture to about 6.8 with citric acid.

Adjusting the intermediate aqueous mixture to between 5.5 and 9.0 may include initially adjusting the pH to about 9.2, optionally with KOH. Adjusting the pH of the intermediate aqueous mixture to between 5.5 and 9.0 may include reducing the pH from about 9.2 to between 5.5 and 9.0, optionally with citric acid, and preferentially to about 6.8.

Adjusting the pH of the intermediate aqueous mixture to between 5.5 and 9.0 may include adjusting the pH to between 6.0 and 7.5. In preferred embodiments, adjusting the pH of the intermediate aqueous mixture to between 5.5 and 9.0 may include adjusting the pH to about 6.8.

Adjusting the intermediate aqueous mixture may include adjusting a salt content of the intermediate aqueous mixture with $MgCl_2$ prior to reducing the pH from about 9.2 to between 5.5 and 9.0.

The initial concentration of lactose in the initial aqueous mixture may be between about 15° Bx and about 63° Bx. In preferred embodiments, the initial concentration of lactose in the initial aqueous mixture may be preferentially in range of 30° Bx to 60 ° Bx.

The initial aqueous mixture may be incubated to produce an intermediate aqueous mixture comprising about 30% to about 40% of the initial concentration of lactose in the initial aqueous mixture.

The initial aqueous mixture may be incubated with the acid lactase until the aqueous mixture comprises 49% to 52% DP2 sugar by weight of total sugar in the intermediate aqueous mixture.

The intermediate aqueous may be incubated with the neutral lactase until the aqueous mixture comprises 23.5% to 25% DP2 sugar by weight of total sugar in the aqueous mixture.

The initial aqueous mixture may be incubated with the acid lactase at a temperature between about 25 and about 75° C., between about 35 and about 65° C., or between about 50 and about 55° C.

The initial aqueous mixture may be incubated with the acid lactase at a pH in a range of 2.5 to 8.0, a range of 3.5 to 6.5, or a range of 4.5 to 5.5.

The intermediate aqueous mixture may be incubated with the neutral lactase at a temperature between about 4° C. and about 50° C., or between about 30° C. and about 45° C.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Definitions

Figure 1:
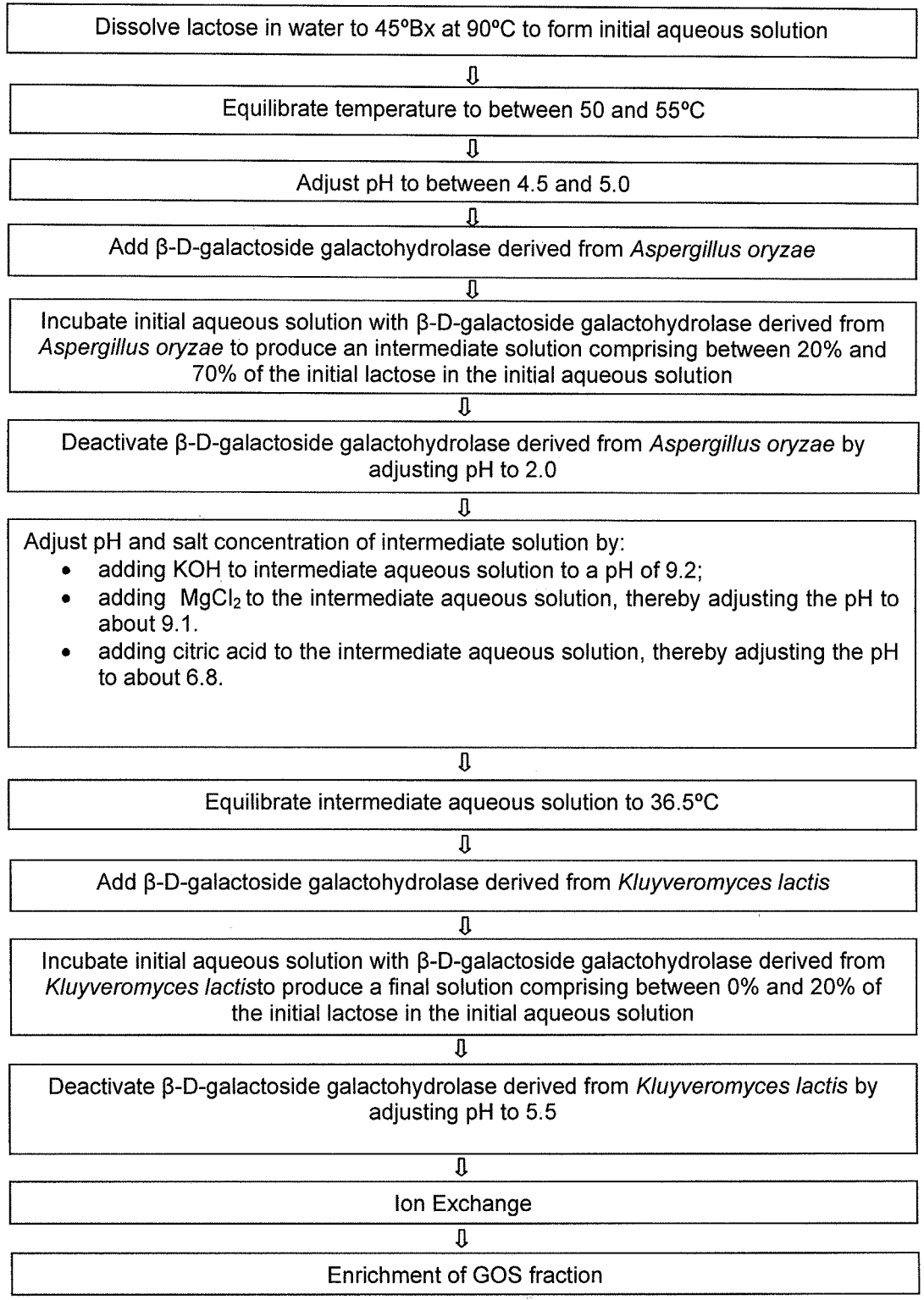
FIG. 1 is a flow diagram of a method of producing GOS syrup as disclosed herein in Example 5.

"DP" as used herein refers to the degree of polymerization of the GOS. A disaccharide GOS is characterized as a "DP2". A trisaccharide GOS is characterized as a "DP3". A tetrasaccharide GOS is characterized as a "DP4". The skilled person will understand that each grouping may include a plurality of species of GOS which differ in terms of the sequence of sugar moieties and the linkages between moieties.

"Consists essentially" as used herein refers to situations in which a feature consists of the recited components except for trace amounts of other possible components (i.e. less than 1%).

"Essentially free" as used herein refers to situations in which a feature does not include any of the absent components as recited except for trace amounts (i.e. less than 1%).

"Initial aqueous solution" as used herein refers to the lactose solution that is prepared for and is digested by the acid fungal lactase as the primarily active lactase.

"Initial concentration of lactose" as used herein refers to the amount of lactose that is added to create the initial aqueous solution, including any lactose that may be added to the initial aqueous solution after incubation with the acid fungal lactase has commenced.

"Intermediate aqueous solution" as used herein refers to the resulting lactose solution upon the effective termination of the digestion of the initial aqueous solution by the acid fungal lactase that is then digested by the yeast neutral lactase.

"Final aqueous solution" as used herein refers to the resulting lactose solution upon the effective termination of the digestion of the intermediate aqueous solution by the yeast neutral lactase.

This disclosure relates to methods of producing galactooligosaccharide (GOS) from lactose using a combination of acidic lactases and neutral lactases. More particularly, the method comprises incubating an aqueous solution comprising lactose with an acid fungal lactase. The acidic fungal lactase hydrolyses the lactose in the solution to galactose and glucose. The lactase further catalyzes transgalactosylation reactions in which the galactosyl moiety is transferred to potentially any sugar moiety present in the solution (e.g. galactose, glucose, lactose, etc.) to produce GOS comprising a mixture of DP2, DP3, DP4, DP5, and even higher order oligosaccharides.

Primary Digestion with an Acid Fungal Lactase

In various embodiments of the methods disclosed herein, the acid fungal lactase is a fungal β-D-galactoside galactohydrolase. The β-D-galactoside galactohydrolase may be derived an *Aspergillus* species. In particular embodiments, the β-D-galactoside galactohydrolase is derived from *Aspergillus oryzae*, such as the β-D-galactoside galactohydrolase available from Enzyme Development Corporation (New York) as ENZECO™ Fungal Lactase Concentrate. The skilled person will understand that the determination of lactase units (LU) will be specified on the TDS for an enzyme. One LU may be defined as that quantity of enzyme which will liberate 1.0 μmol/min of o-nitrophenol under the conditions of the assay specified in the TDS. The concentration of the acid fungal lactase in the initial aqueous solution may be between 1 and 300 LU per gram of lactose in the initial aqueous solution. The concentration of the acid fungal lactase may be between about 10 and about 20 LU per gram of lactose in the initial aqueous solution. The concentration of the acid fungal lactase may be between about 15 and about 17 LU per gram of lactose in the initial aqueous solution. In particular embodiments, the concentration of the acid fungal lactase may be about 16.7 LU per gram of lactose in the initial aqueous solution. In particular embodiments, the concentration of the acid fungal lactase may be about 5.6 LU per gram of lactose in the initial aqueous solution. In particular embodiments, the concentration of the acid fungal lactase may be about 5.8 LU per gram of lactose in the initial aqueous solution. Nevertheless, the skilled person will understand that the methods disclosed herein may be performed with a wide range of acid lactase concentrations depending on a number of factors including the initial concentration of lactose in the aqueous solution, the length of time for which the reaction is allowed to proceed, the pH, and the reaction temperature.

The source of lactose may vary. The lactose can be provided in the form of milk permeate. Alternatively, the lactose can be provided as edible crystalline lactose commonly available from commercial suppliers. The initial concentration of lactose in the initial aqueous solution should be in the range of 15 to 63° Bx. Nevertheless, the skilled person will understand that, for commercial purposes, the initial concentration of lactose should be higher than 15° Bx, as lower concentration of lactose favors hydrolysis over the transgalactosylation, thereby leading to lower GOS yields. Moreover, lower initial concentrations of lactose necessitate larger volumes to be processed in order to obtain the same amount of products, and thus more resources for downstream separation such as chromatographic apparatuses and evaporators. Accordingly, the initial concentration of lactose and in an initial aqueous solution will preferably be between about 30° Bx and about 60° Bx. In particular embodiments, the initial concentration of lactose and in the initial aqueous solution is about 45° Bx. In particular embodiments, the initial concentration of lactose and in the initial aqueous solution is about 53° Bx.

The pH of the initial aqueous solution should be in the range of about 2.5 to about 8.0. The skilled person will understand, however, that the pH of the initial aqueous solution should be close to the optimal pH for the enzyme. Accordingly, in some embodiments, the pH of the initial aqueous solution will be between about 3.5 and about 6.5. In some embodiments, the pH of the initial aqueous solution will be between about 4.5 and about 5.5. For example, ENZECO™ Fungal Lactase Concentrate has activity within a pH range of about 2.5 to about 2.8, although the activity may be slow outside a pH range of about 3.5 to about 6.5. The ENZECO™ Fungal Lactase Concentrate, for example, has a pH optimum of between 4.5 and 5.0.

The skilled person will understand that the pH of a solution comprising lactose may vary depending on the concentration of lactose and the source of lactose. Accordingly, it may be necessary to adjust the pH of the initial aqueous solution within the suitable pH range to bring the pH of the initial aqueous solution within the desired range.

The initial aqueous solution is incubated with the fungal lactase at a temperature between about 35 and about 65° C. ENZECO™ Fungal Lactase Concentrate, for example, has a temperature optimum of 55° C. at pH 4.5 and 6.5. Thus, in some embodiments, the initial aqueous solution is incubated with the acid fungal lactase at a temperature between about 50 and about 56.5° C.

In some embodiments, the initial aqueous solution is incubated with the acid fungal lactase at a temperature between about 50 and about 55° C. In particular embodiments, the initial aqueous solution is incubated with the acid fungal lactase at a temperature of about 53.5° C.

The skilled person will understand that the methods disclosed herein are not limited by any specific reaction time for the incubation of the initial aqueous solution with the acid fungal lactase. Rather, the reaction is allowed to proceed until about 20% to about 70% of the lactose provided in the initial aqueous solution is hydrolyzed (i.e. until the concentration of lactose is between about 20% to about 70% of the initial concentration of lactose in the initial aqueous solution). In particular embodiments, the reaction is allowed to proceed until about 40% of the lactose provided in the initial aqueous solution is hydrolyzed (i.e. until the concentration of lactose is about 40% of the initial concentration of lactose in the initial aqueous solution) and/or until DP2 sugars comprise 49% to 52% (w/w) of total sugar in the intermediate aqueous solution. Accordingly, the concentration of lactose and other sugars in the initial aqueous solution may be monitored from time to time in order to identify an appropriate time to end the incubation with the acid fungal lactase. The skilled person will understand that incubation time depends on a combination of temperature, initial lactose concentration, pH, and lactase concentration. Reactions may be run quickly with a large concentration of enzyme if enzyme cost in not important. Alternatively, enzyme costs may be saved if a reaction is carried out more slowly. Parameters may also be adjusted depending on how the reaction time is to be logistically tied in downstream processes.

Secondary Digestion with a Neutral Yeast Lactase

Once the desired concentration of lactose in the aqueous solution (and/or a DP2 sugar concentration of about 49% to 52% (w/w) of total sugar in the intermediate aqueous solution) is achieved, this intermediate aqueous solution is incubated with a yeast neutral lactase. Prior to adding the yeast neutral lactase, it may be preferable to deactivate the acid fungal lactase. Deactivating the acid fungal lactase may involve adjusting the pH of the intermediate aqueous solution to about 2 or less with, for example, HCl. Deactivating the acid fungal lactase seeks to minimize hydrolysis of GOS by the acid fungal lactase, and thereby maximize GOS yield. However, the skilled person will understand that active steps to deactivate of the acid fungal lactase may not be completely necessary.

The neutral yeast lactase is added to the intermediate aqueous solution comprising GOS and about 20 to about 70% of the initial lactose to a concentration. In various embodiments of the methods disclosed herein, the neutral yeast lactase is a yeast β-D-galactoside galactohydrolase. The β-D-galactoside galactohydrolase may be derived from a *Kluyveromyces* species. In particular embodiments, the β-D-galactoside galactohydrolase is derived from *Kluyveromyces lactis*, such as the β-D-galactoside galactohydrolase available from Enzyme Development Corporation (New York) as ENZECO™ Lactase NL 2.5X. The yeast neutral lactase may be added to the intermediate aqueous solution at a concentration of between 1 and 50 LU per gram of lactose in the intermediate aqueous solution. The yeast neutral lactase may be added to the intermediate aqueous solution at a concentration of about 4 to about 5 LU/g lactose in the intermediate aqueous solution. The yeast neutral lactase may be added to the intermediate aqueous solution at a concentration of about 4.7 LU per gram of lactose in the intermediate aqueous solution. The yeast neutral lactase may be added to the intermediate aqueous solution at a concentration of about 4.4 LU per gram of lactose in the intermediate aqueous solution. Nevertheless, the skilled person will understand that the methods disclosed herein may be performed with a wide range of yeast lactase concentrations depending on a number of factors including the initial concentration of lactose in the intermediate aqueous solution, the length of time for which the reaction is allowed to proceed, the pH, and the reaction temperature.

In certain embodiments, e.g. where the neutral yeast β-D-galactoside galactohydrolase is derived from a *Kluyveromyces* species, it may be necessary to add potassium and magnesium for enzyme activity. In embodiments where the pH must be adjusted up to 5.5 or higher, e.g. where the pH of the intermediate aqueous solution has been adjusted to about 2.0 or zero or less to deactivate the acid fungal lactase, the pH and salt can be adjusted using potassium, magnesium chloride, and citric acid.

ENZECO™ Lactase NL 2.5X has a pH optimum of about 6 to about 7. Accordingly, the skilled person will understand that it may be necessary to adjust the pH of the intermediate aqueous solution between 6 and 7.5 to facilitate the activity of the neutral yeast lactase. In particular embodiments, adjusting pH of the intermediate solution with potassium hydroxide, magnesium chloride and citric acid involves adjusting the pH to about 6.8.

Such pH adjustments can lead to turbidity of the mixture, which can plug downstream separation equipment. However, this turbidity can largely be avoided by adding the salts in a specific sequence. More particularly, adjusting the pH of the intermediate aqueous solution to the desired pH and salt concentration by sequentially adding the potassium hydroxide, magnesium chloride and citric acid can avoid turbidity. More particularly, sequentially adding potassium hydroxide, magnesium chloride and citric acid to the intermediate aqueous solution in the following amount and order can largely avoid turbidity:

adding potassium hydroxide to arrive at a pH of about 9.2;
adding magnesium chloride to arrive at a pH of about 9.1; and
adding citric acid to a pH of about 6.8.

The temperature of the intermediate aqueous solution is adjusted to between 30 and 45° C. prior to addition of the neutral yeast lactase. However, the skilled person will understand that while temperature may be adjusted for optimal enzyme activity, the yeast lactase may perform at a much slower rate outside this range, e.g. between about 4.0 and about 50.0° C. In particular embodiments disclosed herein, the temperature of the intermediate aqueous solution is adjusted to about 36.5° C. for incubation with the neutral yeast lactase. As with the acid fungal lactase, the reaction time will depend on temperature, pH, lactase concentration, and initial concentration of lactose in the intermediate aqueous solution. Again, the reaction rate can be increased if enzyme cost is not a concern. Alternatively, the reactions may be run more slowly to save on the cost of enzyme.

The intermediate aqueous solution is incubated with the neutral yeast lactase to produce a final aqueous solution in which the concentration of lactose is between zero and about 20% of the initial concentration of lactose in the initial aqueous solution. In some embodiments, the intermediate aqueous solution is incubated with the neutral yeast lactase until a final aqueous solution comprising 23.5% to 25% DP2 sugar (w/w) of total sugar in the final aqueous solution is achieved.

Deactivation of the Yeast Lactase

Once a final concentration of between zero and 20% of the initial concentration of lactose and the initial aqueous solution has been achieved, the neutral yeast lactase may be deactivated. In some embodiments, deactivating the neutral yeast lactase involves adjusting the pH of the final aqueous solution to about pH 5.5, at or below which pH the enzyme effectively has no activity. In addition to adjusting the pH to 5.5, or as an alternative to adjusting pH to 5.5, deactivating the yeast lactase may involve incubating the final aqueous solution at 72° C. The necessity of the pH adjustment step may depend on how quickly the final aqueous solution can be heated, and how quickly the reaction is proceeding prior to such heat treatment. If heating can be accomplished quickly enough so that there is no change in sugar composition (e.g. hydrolysis of GOS) while the final aqueous solution is being heated, then a pH adjustment may be unnecessary. On the other hand, the skilled person will appreciate that it may be unnecessary to heat treat the final aqueous solution to deactivate the neutral yeast lactase if pH is used to deactivate the reaction, the reaction rate is very slow, or the enzyme a little to no activity remaining.

Separation

Chromatography may then be used to remove the enzymes, stabilizing agents, glucose and galactose from the final aqueous solution to produce a GOS-enriched solution. Ion exchange chromatography may be initially carried out on the final aqueous solution to remove the lactase enzymes, cations, anions, and components contributing to color.

After ion exchange, the further separation may be conducted to partially remove glucose and galactose and enrich the GOS fraction. The skilled person will be aware of the standard methods that may be available, including ion exchange, filtration, chromatographic separation (SMB), or additional fermentation reactions.

For example, simulated moving bed chromatography may be used to enrich the GOS in the GOS syrup from about 40% w/w of total carbohydrate in the final aqueous solution to greater than 60% w/w of total carbohydrates after separation.

GOS Products

The composition of different GOS species in a GOS syrup is unpredictable and will depend on the source of lactase with which lactose solution is incubated, the concentration of lactose, and the concentration of lactose. Accordingly, the skilled person will appreciate that the GOS syrups disclosed herein have a unique balance of di-(DP2), tri-(DP3), tetra-(DP4), penta-(DP5) and higher GOS. Accordingly, this disclosure also relates to GOS syrups with novel GOS balances that are produced according to methods disclosed herein.

Accordingly, this disclosure further relates to use of the combination of a first β-D-galactoside galactohydrolase derived from an *Aspergillus oryzae* with a second β-D-galactoside galactohydrolase derive from a *Kluyveromyces lactis* in the preparation of GOS compositions, e.g. GOS syrups, from an aqueous solution comprising lactose. The GOS syrup may comprise at least 40% GOS w/w of total carbohydrate in the GOS syrup. The use involves incubation of the aqueous solution with the first β-D-galactoside galactohydrolase followed by incubation with the second β-D-galactoside galactohydrolase.

For the purposes of this application, "GOS compositions" include "GOS syrup" and GOS "preparations" as discussed below.

GOS Syrups Containing β-D-Galp-(1→3)-D-Galp

For example, various embodiments of galactooligosaccharide (GOS) syrup that are made according to the methods disclosed herein comprising β-D-Galp-(1→3)-D-Galp.

Such GOS syrup may further comprise: galactose; glucose; β-D-Galp-(1→6)-D-Galp, β-D-Galp-(1→3)-D-Glcp, β-D-Galp-(1→4)-D-Glcp, β-D-Galp-(1→6)-β-D-Galp-(1→4)-D-Glcp, β-D-Galp-(1→2)-D-Glcp, β-D-Galp-(1→3)-DGlcp, β-D-Galp-(1→4)-β-D-Galp-(1→4)-D-Glcp, β-D-Galp-(1→3)-β-D-Galp-(1→4)-D-Glop; β-D-Galp-(1→6)-β-D-Galp-(1→6)-β-D-Galp-(1→4)-D-Glcp, β-D-Galp-(1→6)-β-D-Galp-(1→3)-β-D-Galp-(1→4)-D-Glcp, β-D-Galp-(1→6)-β-D-Galp-(1→4)-β-D-Galp-(1→4)-D-Glcp, or any combination thereof.

Such GOS syrup may be essentially free of: β-D-Galp-(1→4)-[β-D-Galp-(1→6)-]D-Glcp; β-D-Galp-(1→4)-D-Galp; β-D-Galp-(1→2)-[β-D-Galp-(1→4)-]D-Glcp; β-D-Galp-(1→2)-[β-D-Galp-(1→6)-]D-Glcp; β-D-Galp-(1→3)-[β-D-Galp-(1→6)-]D-Glcp; β-D-Galp-(1→4)-β-D-Galp-(1→2)-D-Glcp; β-D-Galp-(1→4)-β-D-Galp-(1→3)-D-Glcp; β-D-Galp-(1→4)-[β-D-Galp-(1→4)-β-D-Galp-(1→6)-]D-Glcp; β-D-Galp-(1→4)-β-D-Galp-(1→4)-[β-D-Galp-(1→6)-]D-Glcp; β-D-Galp-(1→4)-β-D-Galp-(1→4)-[β-D-Galp-(1→2)-]D-Glcp; β-D-Galp-(1→4)-β-D-Galp-(1→2)-[β-D-Galp-(1→4)-]D-Glcp; β-D-Galp-(1→4)-β-D-Galp-(1→2)-[β-D-Galp-(1→6)-]D-Glcp; β-D-Galp-(1→4)-β-D-Galp-(1→6)-[β-D-Galp-(1→2)-]D-Glcp; β-D-Galp-(1→4)-β-D-Galp-(1→4)-β-D-Galp-(1→6)-D-Glcp; β-D-Galp-(1→4)-β-D-Galp-(1→4)-βD-Galp-(143 4)-D-Glcp; β-D-Galp-(1→4)-β-D-Galp-(1→4)-β-D-Galp-(1→2)-D-Glcp; β-D-Galp-(1→4)-β-D-Galp-(1→4)-β-D-Galp-(1→3)-D-Glcp; β-D-Galp-(1→6)-β-D-Galp-(1→3)-D-Glcp; β-D-Galp-(1→6)-β-D-Galp-(1→4)-β-D-Galp-(1→3)-D-Glcp; β-D-Galp-(1→3)-β-D-Galp-(1→6)-D-Glcp; β-D-Galp-(1→3)-β-D-Galp-(1→3)-D-Glcp; β-D-Galp-(1→3)-β-D-Galp-(1→2)-D-Glcp; β-D-Galp-(1→3)-β-D-Galp-(1→3)-β-D-Galp-(1→3)-β-D-Galp-(1→4)-D-Glcp; β-D-Galp-(1→3)-β-D-Galp-(1→3)-β-D-Galp-(1→3)-D-Glcp; β-D-Galp-(1→3)-β-D-Galp-(1→3)-β-D-Galp-(1→2)-D-Glcp; β-D-Galp-(1→3)-β-D-Galp-(1→6)-β-D-Galp-(1→4)-D-Glcp; β-D-Galp-(1→3)-[β-D-Galp-(1→6)-]β-D-Galp-(1→4)-D-Glcp; or any combination thereof.

In some embodiments, essentially all tetrasaccharides in a tetrasaccharide fraction of the GOS syrup, if present, include a β-D-Galp-(1→6)-linkage. The tetrasaccharide fraction may consist essentially of: β-D-Galp-(1→6)-β-D-Galp-(1→6)-β-D-Galp-(1→4)-D-Glcp; β-D-Galp-(1→6)-β-D-Galp-(1→3)-β-D-Galp-(1→4)-D-Glcp; β-D-Galp-(1→6)-β-D-Galp-(1→4)-β-D-Galp-(1→4)-D-Glcp; or any combination thereof.

In some embodiments, essentially all trisaccharides in a trisaccharide fraction of the GOS syrup, if present, are linear. Each trisaccharide may terminate with a β-D-Galp-(1→4)-D-Glcp linkage. The trisaccharide fraction may consist essentially of: β-D-Galp-(1→6)-β-D-Galp-(1→4)-D-Glcp; β-D-Galp-(1→3)-β-D-Galp-(1→4)-D-Glcp; β-D-Galp-(1→4)-β-D-Galp-(1→4)-D-Glcp; or any combination thereof.

GOS Syrup Containing a Tetrasaccharide Fraction Consisting Essentially of Tetrasaccharides with a β-D-Galp-(1→6)-linkage Various embodiments of galactooligosaccharide (GOS) syrup that are made according to the methods disclosed herein contain a tetrasaccharide fraction in which essentially all tetrasaccharides include a β-D-Galp-(1→6)-linkage. The tetrasaccharide fraction may consist essentially of: β-D-Galp-(1→6)-β-D-Galp-(1→6)-β-D-Galp-(1→4)-D-Glcp; β-D-Galp-(1→6)-β-D-Galp-(1→3)-β-D-Galp-(1→4)-D-Glcp; β-D-Galp-(1→6)-β-D-Galp-(1→4)-β-D-Galp-(1→4)-D-Glcp; or any combination thereof.

Such GOS syrup may also include a trisaccharide fraction wherein essentially all trisaccharides in the trisaccharide fraction of the GOS syrup are linear. Each trisaccharide may terminate with a β-D-Galp-(1→4)-D-Glcp linkage. The trisaccharide fraction may consist essentially of: β-D-Galp-(1→6)-β-D-Galp-(1→4)-D-Glcp; β-D-Galp-(1→3)-β-D-Galp-(1→4)-D-Glcp; β-D-Galp-(1→4)-β-D-Galp-(1→4)-D-Glcp, or any combination thereof.

Such GOS syrup may further comprise β-D-Galp-(1→3)-D-Galp.

Such GOS syrup may be essentially free of: β-D-Galp-(1→4)-[β-D-Galp-(1→6)-]D-Glcp; β-D-Galp-(1→4)-D-Galp; β-D-Galp-(1→2)-[β-D-Galp-(1→4)-]D-Glcp; β-D-Galp-(1→2)-[β-D-Galp-(1→6)-]D-Glcp; β-D-Galp-(1→3)-[β-D-Galp-(1→6)-]D-Glcp; β-D-Galp-(1→4)-β-D-Galp-(1→2)-D-Glcp; β-D-Galp-(1→4)-β-D-Galp-(1→3)-D-Glcp; β-D-Galp-(1→4)-[β-D-Galp-(1→4)-β-D-Galp-(1→6)-]D-Glcp; β-D-Galp-(1→4)-β-D-Galp-(1→4)-[β-D-Galp-(1→6)-]D-Glcp; β-D-Galp-(1→4)-β-D-Galp-(1→4)-[β-D-Galp-(1→2)-]D-Glcp; β-D-Galp-(1→4)-β-D-Galp-(1→2)-[β-D-Galp-(1→4)-]D-Glcp; β-D-Galp-(1→4)-β-D-Galp-(1→2)-[β-D-Galp-(1→6)-]D-Glcp; β-D-Galp-(1→4)-β-D-Galp-(1→6)-[β-D-Galp-(1→2)-]D-Glcp; β-D-Galp-(1→4)-β-D-Galp-(1→4)-β-D-Galp-(1→6)-D-Glcp; β-D-Galp-(1→4)-β-D-Galp-(1→4)-β-D-Galp-(1→4)-D-Glcp; β-D-Galp-(1→4)-β-D-Galp-(1→4)-β-D-Galp-(1→2)-D-Glcp; β-D-Galp-(1→4)-β-D-Galp-(1→4)-β-D-Galp-(1→3)-D-Glcp; β-D-Galp-(1→6)-β-D-Galp-(1→3)-D-Glcp; β-D-Galp-(1→6)-β-D-Galp-(1→4)-β-D-Galp-(1→3)-D-Glcp; β-D-Galp-(1→3)-β-D-Galp-(1→6)-D-Glcp; β-D-Galp-(1→3)-β-D-Galp-(1→3)-D-Glcp; β-D-Galp-(1→3)-β-D-Galp-(1→2)-D-Glcp; β-D-Galp-(1→3)-β-D-Galp-(1→3)-β-D-Galp-(1→4)-D-Glcp; β-D-Galp-(1→3)-β-D-Galp-(1→3)-β-D-Galp-(1→3)-D-Glcp; β-D-Galp-(1→3)-β-D-Galp-(1→3)-β-D-Galp-(1→2)-D-Glcp; β-D-Galp-(1→3)-β-D-Galp-(1→6)-β-D-Galp-(1→4)-D-Glcp; β-D-Galp-(1→3)-[β-DGalp-(1→6)-]β-D-Galp-(1→4)-D-Glcp; or any combination thereof.

In particular embodiments, such GOS syrup may be essentially free of β-D-Galp-(1→3)-[β-DGalp-(1→6)-]β-D-Galp-(1→4)-D-Glcp; β-D-Galp-(1→3)-β-D-Galp-(1→6)-β-D-Galp-(1→4)-D-Glcp, β-D-Galp-(1→3)-β-D-Galp-(1→3)-β-D-Galp-(1→4)-D-Glcp, or any combination thereof.

GOS Syrup Containing a Trisaccharide Fraction Consisting Essentially of Linear Trisaccharides Various embodiments of galactooligosaccharide (GOS) syrup that are made according to the methods disclosed herein contain a trisaccharide fraction, wherein essentially all trisaccharides in the trisaccharide fraction are linear. Each trisaccharide terminates with a β-D-Galp-(1→4)-D-Glcp linkage. The trisaccharide fraction may consist essentially of: β-D-Galp-(1→6)-β-D-Galp-(1→4)-D-Glcp; β-D-Galp-(1→3)-β-D-Galp-(1→4)-D-Glcp; β-D-Galp-(1→4)-β-D-Galp-(1→4)-D-Glcp, or any combination thereof.

Such GOS syrup may also include a tetrasaccharide fraction in which essentially all tetrasaccharides include a β-D-Galp-(1→6)-linkage. The tetrasaccharide fraction may consist essentially of: β-D-Galp-(1→6)-β-D-Galp-(1→6)-β-D-Galp-(1→4)-D-Glcp; β-D-Galp-(1→6)-β-D-Galp-(1→3)-β-D-Galp-(1→4)-D-Glcp; β-D-Galp-(1→6)-β-D-Galp-(1→4)-β-D-Galp-(1→4)-D-Glcp; or any combination thereof.

Such GOS syrup may further comprise β-D-Galp-(1→3)-D-Galp.

Such GOS syrup may be essentially free of: β-D-Galp-(1→4)-[β-D-Galp-(1→6)-]D-Glcp; β-D-Galp-(1→4)-D-Galp; β-D-Galp-(1→2)-[β-D-Galp-(1→4)-]D-Glcp; β-D-Galp-(1→2)-[β-D-Galp-(1→6)-]D-Glcp; β-D-Galp-(1→3)-[β-D-Galp-(1→6)-]D-Glcp; β-D-Galp-(1→4)-β-D-Galp-(1→2)-D-Glcp; β-D-Galp-(1→4)-β-D-Galp-(1→3)-D-Glcp; β-D-Galp-(1→4)-[β-D-Galp-(1→4)-β-D-Galp-(1→6)-]D-Glcp; β-D-Galp-(1→4)-β-D-Galp-(1→4)-[β-D-Galp-(1→6)-]D-Glcp; β-D-Galp-(1→4)-β-D-Galp-(1→4)-[β-D-Galp-(1→2)-]D-Glcp; β-D-Galp-(1→4)-β-D-Galp-(1→2)-[β-D-Galp-(1→4)-]D-Glcp; β-D-Galp-(1→4)-β-D-Galp-(1→2)-[β-D-Galp-(1→6)-]D-Glcp; β-D-Galp-(1→4)-β-D-Galp-(1→6)-[β-D-Galp-(1→2)-]D-Glcp; β-D-Galp-(1→4)-β-D-Galp-(1→4)-β-D-Galp-(1→6)-D-Glcp; β-D-Galp-(1→4)-β-D-Galp-(1→4)-β-D-Galp-(1→4)-D-Glcp; β-D-Galp-(1→4)-β-D-Galp-(1→4)-β-D-Galp-(1→2)-D-Glcp; β-D-Galp-(1→4)-β-D-Galp-(1→4)-β-D-Galp-(1→3)-D-Glcp; β-D-Galp-(1→6)-β-D-Galp-(1→3)-D-Glcp; β-D-Galp-(1→6)-β-D-Galp-(1→4)-β-D-Galp-(1→3)-D-Glcp; β-D-Galp-(1→3)-β-D-Galp-(1→6)-D-Glop; β-D-Galp-(1→3)-β-D-Galp-(1→3)-D-Glcp; β-D-Galp-(1→3)-β-D-Galp-(1→2)-D-Glcp; β-D-Galp-(1→3)-β-D-Galp-(1→3)-β-D-Galp-(1→4)-D-Glcp; β-D-Galp-(1→3)-β-D-Galp-(1→3)-β-D-Galp-(1→3)-D-Glcp; β-D-Galp-(1→3)-β-D-Galp-(1→3)-β-D-Galp-(1→2)-D-Glcp; β-D-Galp-(1→3)-β-D-Galp-(1→6)-β-D-Galp-(1→4)-D-Glcp; β-D-Galp-(1→3)-[β-DGalp-(1→6)-]β-D-Galp-(61→4)-D-Glop; or any combination thereof.

In particular embodiments, such GOS syrup may be essentially free of β-D-Galp-(1→3)-[β-DGalp-(1→6)-]β-D-Galp-(1→4)-D-Glcp, β-D-Galp-(1→3)-β-D-Galp-(1→6)-β-D-Galp-(1→4)-D-Glcp, β-D-Galp-(1→3)-β-D-Galp-(1→3)-β-D-Galp-(1→4)-D-Glcp, or any combination thereof.

GOS syrup containing a tetrasaccharide fraction consisting essentially of one or more of β-D-Galp-(1→6)-β-D-Galp-(1→6)-β-D-Galp-(1→4)-D-Glcp, β-D-Galp-(1→6)-β-D-Galp-(1→3)-β-D-Galp-(1→4)-D-Glcp, and β-D-Galp-(1→6)-β-D-Galp-(1→4)-β-D-Galp-(1→4)-D-Glcp Various embodiments of galactooligosaccharide (GOS) syrup that are made according to the methods disclosed herein comprise: β-D-Galp-(1→6)-β-D-Galp-(1→6)-β-D-Galp-(1→4)-D-Glcp; β-D-Galp-(1→6)-β-D-Galp-(1→3)-β-D-Galp-(1→4)-D-Glcp; β-D-Galp-(1→6)-β-D-Galp-(1→4)-β-D-Galp-(1→4)-D-Glcp; or any combination thereof. However, such GOS syrup is also essentially free of one or more of: β-D-Galp-(1→4)-[β-D-Galp-(1→6)-]D-Glcp; β-D-Galp-(1→4)-D-Galp; β-D-Galp-(1→2)-[β-D-Galp-(1→4)-]D-Glcp; β-D-Galp-(1→2)-[β-D-Galp-(1→6)-]D-Glcp; β-D-Galp-(1→3)-[β-D-Galp-(1→6)-]D-Glop; β-D-Galp-(1→4)-β-D-Galp-(1→2)-D-Glcp; β-D-Galp-(1→4)-β-D-Galp-(1→3)-D-Glcp; β-D-Galp-(1→4)-[β-D-Galp-(1→4)-β-D-Galp-(1→6)-]D-Glcp; β-D-Galp-(1→4)-β-D-Galp-(1→4)-[β-D-Galp-(1→6)-]D-Glcp; β-D-Galp-(1→4)-β-D-Galp-(1→4)-[β-D-Galp-(1→2)-]D-Glcp; β-D-Galp-(1→4)-β-D-Galp-(1→2)-[β-D-Galp-(1→4)-]D-Glcp; β-D-Galp-(1→4)-β-D-Galp-(1→2)-[β-D-Galp- (1→6)-]D-Glcp; β-D-Galp-(1→4)-β-D-Galp-(1→6)-[β-D-Galp-(1→2)-]D-Glcp; β-D-Galp-(1→4)-β-D-Galp-(1→4)-β-D-Galp-(1→6)-D-Glcp; β-D-Galp-(1→4)-β-D-Galp-(1→4)-β-D-Galp-(1→4)-D-Glcp; β-D-Galp-(1→4)-β-D-Galp-(1→4)-β-D-Galp-(1→2)-D-Glcp; β-D-Galp-(1→4)-β-D-Galp-(1→4)-β-D-Galp-(1→3)-D-Glcp; β-D-Galp-(1→6)-β-D-Galp-(1→3)-D-Glcp; β-D-Galp-(1→6)-β-D-Galp-(1→4)-β-D-Galp-(1→3)-D-Glcp; β-D-Galp-(1→3)-β-D-Galp-(1→6)-D-Glcp; β-D-Galp-(1→3)-β-D-Galp-(1→3)-D-Glcp; β-D-Galp-(1→3)-β-D-Galp-(1→2)-D-Glcp; β-D-Galp-(1→3)-β-D-Galp-(1→3)-β-D-Galp-(1→4)-D-Glcp; β-D-Galp-(1→3)-β-D-Galp-(1→3)-β-D-Galp-(1→3)-D-Glcp; β-D-Galp-(1→3)-β-D-Galp-(1→3)-β-D-Galp-(1→2)-D-Glcp; β-D-Galp-(1→3)-β-D-Galp-(1→6)-β-D-Galp-(1→4)-D-Glcp; β-D-Galp-(1→3)-[β-DGalp-(1→6)-]β-D-Galp-(1→4)-D-Glcp; or any combination thereof.

In some embodiments, essentially all trisaccharides in a trisaccharide fraction of the GOS syrup, if present, are linear. Each trisaccharide may terminate with a β-D-Galp-(1→4)-D-Glcp linkage. The trisaccharide fraction may consist essentially of: β-D-Galp-(1→6)-β-D-Galp-(1→4)-D-Glcp; β-D-Galp-(1→3)-β-D-Galp-(1→4)-D-Glcp; β-D-Galp-(1→4)-β-D-Galp-(1→4)-D-Glcp; or any combination thereof.

In some embodiments, the GOS syrup may further include β-D-Galp-(1→3)-D-Galp.

GOS syrup containing a tetrasaccharide fraction consisting essentially of one or both of β-D-Galp-(1→6)-β-D-Galp-(1→6)-β-D-Galp-(1→4)-D-Glcp and β-D-Galp-(1→6)-β-D-Galp-(1→3)-β-D-Galp-(1→4)-D-Glcp Various embodiments of galactooligosaccharide (GOS) syrup that are made according to the methods disclosed herein comprise β-D-Galp-(1→6)-β-D-Galp-(1→6)-β-D-Galp-(1→4)-D-Glcp, β-D-Galp-(1→6)-β-D-Galp-(1→3)-β-D-Galp-(1→4)-D-Glcp, or both, but are essentially free of: β-D-Galp-(1→3)-[β-DGalp-(1→6)-]β-D-Galp-(1→4)-D-Glcp; β-D-Galp-(1→3)-β-D-Galp-(1→6)-β-D-Galp-(1→4)-D-Glcp; β-D-Galp-(1→3)-β-D-Galp-(1→3)-β-D-Galp-(1→4)-D-Glcp; or any combination thereof.

In some embodiments, essentially all trisaccharides in a trisaccharide fraction of the GOS syrup, if present, are linear. Each trisaccharide may terminate with a β-D-Galp-(1→4)-D-Glcp linkage. The trisaccharide fraction may consist essentially of: β-D-Galp-(1→6)-β-D-Galp-(1→4)-D-Glcp; β-D-Galp-(1→3)-β-D-Galp-(1→4)-D-Glcp; β-D-Galp-(1→4)-β-D-Galp-(1→4)-D-Glcp; or any combination thereof.

In some embodiments, the GOS syrup may further include β-D-Galp-(1→3)-D-Galp.

Preparations

GOS syrup made according to the methods disclosed herein may be further dehydrated, refined, purified or partially purified, and/or separated into fractions based on degree of polymerization (DP). Moreover, specific galactooligosaccharides may be isolated from the GOS syrup. Fractions and/or isolated galactooligosaccharides may also be recombined. Such further processed GOS syrup products, may be referred to generally as "preparations" or "compositions".

Preparations Containing a Tetrasaccharide Fraction Consisting Essentially of Tetrasaccharides with a β-D-Galp-(1→6)-Linkage Various embodiments of preparation from GOS syrup that are made according to the methods disclosed herein comprise a tetrasaccharide fraction wherein essentially all tetrasaccharides in the tetrasaccharide fraction include a β-D-Galp-(1→6)-linkage. The tetrasaccharide fraction may consist essentially of: β-D-Galp-(1→6)-β-D-Galp-(1→6)-β-D-Galp-(1→4)-D-Glcp; β-D-Galp-(1→6)-β-D-Galp-(1→3)-β-D-Galp-(1→4)-D-Glcp; β-D-Galp-(1→6)-β-D-Galp-(1→4)-β-D-Galp-(1→4)-D-Glcp; or any combination thereof.

The preparation may further include a trisaccharide fraction, wherein essentially all trisaccharides in the trisaccharide fraction are linear. Each trisaccharide may terminate with a β-D-Galp-(1→4)-D-Glcp linkage. The trisaccharide fraction may consist essentially of: β-D-Galp-(1→6)-β-D-Galp-(1→4)-D-Glcp; β-D-Galp-(1→3)-β-D-Galp-(1→4)-D-Glcp; β-D-Galp-(1→4)-β-D-Galp-(1→4)-D-Glcp; or any combination thereof.

The preparation may further include β-D-Galp-(1→3)-D-Galp.

Preparations Containing a Trisaccharide Fraction Consisting Essentially of Linear Trisaccharides Various embodiments of preparation from GOS syrup that are made according to the methods disclosed herein comprise a trisaccharide fraction, wherein essentially all trisaccharides in the trisaccharide fraction are linear. Each trisaccharide may terminate with a β-D-Galp-(1→4)-D-Glcp linkage. The trisaccharide fraction may consist essentially of: β-D-Galp-(1→6)-β-D-Galp-(1→4)-D-Glcp; β-D-Galp-(1→3)-β-D-Galp-(1→4)-D-Glcp; β-D-Galp-(1→4)-β-D-Galp-(1→4)-D-Glcp; or any combination thereof.

The preparation may further include a tetrasaccharide fraction, wherein essentially all tetrasaccharides in the tetrasaccharide fraction include a β-D-Galp-(1→6)-Linkage. The tetrasaccharide fraction may consist essentially of: β-D-Galp-(1→6)-β-D-Galp-(1→6)-β-D-Galp-(1→4)-D-Glcp; β-D-Galp-(1→6)-β-D-Galp-(1→3)-β-D-Galp-(1→4)-D-Glcp; β-D-Galp-(1→6)-β-D-Galp-(1→4)-β-D-Galp-(1→4)-D-Glcp, or any combination thereof.

The preparation may further include β-D-Galp-(1→3)-D-Galp.

Preparations Containing β-D-Galp-(1→3)-D-Galp

Various embodiments of preparation from GOS syrup that are made according to the methods disclosed herein comprise β-D-Galp-(1→3)-D-Galp. The preparation may further include a tetrasaccharide fraction, wherein essentially all tetrasaccharides in the tetrasaccharide fraction include a β-D-Galp-(1→6)-linkage. The tetrasaccharide fraction may consist essentially of: β-D-Galp-(1→6)-β-D-Galp-(1→6)-β-D-Galp-(1→4)-D-Glcp; β-D-Galp-(1→6)-β-D-Galp-(1→3)-β-D-Galp-(1→4)-D-Glcp; β-D-Galp-(1→6)-β-D-Galp-(1→4)-β-D-Galp-(1→4)-D-Glcp; or any combination thereof.

The preparation may further include a trisaccharide fraction, wherein essentially all trisaccharides in the trisaccharide fraction are linear. Each trisaccharide may terminate with a β-D-Galp-(1→4)-D-Glcp linkage. The trisaccharide fraction may consist essentially of: β-D-Galp-(1→6)-β-D-Galp-(1→4)-D-Glcp; β-D-Galp-(1→3)-β-D-Galp-(1→4)-D-Glcp; β-D-Galp-(1→4)-β-D-Galp-(1→4)-D-Glcp; or any combination thereof.

Each of the preparations described above may be essentially free of: β-D-Galp-(1→4)-[β-D-Galp-(1→6)-]D-Glcp; β-D-Galp-(1→4)-D-Galp; β-D-Galp-(1→2)-[β-D-Galp-(1→4)-]D-Glcp; β-D-Galp-(1→2)-[β-D-Galp-(1→6)-]D-Glcp; β-D-Galp-(1→3)-[β-D-Galp-(1→6)-]D-Glcp; β-D-Galp-(1→4)-β-D-Galp-(1→2)-D-Glcp; β-D-Galp-(1→4)-β-D-Galp-(1→3)-D-Glcp; β-D-Galp-(1→4)-[β-D-Galp-(1→4)-β-D-Galp-(1→6)-]D-Glcp; β-D-Galp-(1→4)-β-D-Galp-(1→4)-[β-D-Galp-(1→6)-]D-Glcp; β-D-Galp-(1→4)-β-D-Galp-(1→4)-[β-D-Galp-(1→2)-]D-Glcp; β-D-Galp- (1→4)-β-D-Galp-(1→2)-[β-D-Galp-(1→4)-]D-Glcp; β-D-Galp-(1→4)-β-D-Galp-(1→2)-[β-D-Galp-(1→6)-]D-Glcp; β-D-Galp-(1→4)-β-D-Galp-(1→6)-[β-D-Galp-(1→2)-]D-Glcp; β-D-Galp-(1→4)-β-D-Galp-(1→4)-β-D-Galp-(1→6)-D-Glcp; β-D-Galp-(1→4)-β-D-Galp-(1→4)-β-D-Galp-(1→4)-D-Glcp; β-D-Galp-(1→4)-β-D-Galp-(1→4)-β-D-Galp-(1→2)-D-Glcp; β-D-Galp-(1→4)-β-D-Galp-(1→4)-β-D-Galp-(1→3)-D-Glcp; β-D-Galp-(1→6)-β-D-Galp-(1→3)-D-Glcp; β-D-Galp-(1→6)-β-D-Galp-(1→4)-β-D-Galp-(1→3)-D-Glcp; β-D-Galp-(1→3)-β-D-Galp-(1→6)-D-Glcp; β-D-Galp-(1→3)-β-D-Galp-(1→3)-D-Glcp; β-D-Galp-(1→3)-β-D-Galp-(1→2)-D-Glcp; β-D-Galp-(1→3)-β-D-Galp-(1→3)-β-D-Galp-(1→4)-D-Glcp; β-D-Galp-(1→3)-β-D-Galp-(1→3)-β-D-Galp-(1→3)-D-Glcp; β-D-Galp-(1→3)-β-D-Galp-(1→3)-β-D-Galp-(1→2)-D-Glcp; β-D-Galp-(1→3)-β-D-Galp-(1→6)-β-D-Galp-(1→4)-D-Glcp; β-D-Galp-(1→3)-[β-D-Galp-(1→6)-]β-D-Galp-(1→4)-D-Glcp; or any combination thereof.

Each of the preparations described above may be essentially free of β-D-Galp-(1→3)-[β-DGalp-(1→6)-]β-D-Galp-(1→4)-D-Glcp; β-D-Galp-(1→3)-β-D-Galp-(1→6)-β-D-Galp-(1→4)-D-Glcp, β-D-Galp-(1→3)-β-D-Galp-(1→3)-β-D-Galp-(1→4)-D-Glcp, or any combination thereof.

Preparations Containing a Tetrasaccharide Fraction Consisting Essentially of One or More of β-D-Galp-(1→6)-β-D-Galp-(1→6)-β-D-Galp-(1→4)-D-Glcp, β-D-Galp-(1→6)-β-D-Galp-(1→3)-β-D-Galp-(1→4)-D-Glcp, and β-D-Galp-(1→6)-β-D-Galp-(1→4)-β-D-Galp-(1→4)-D-Glcp Various embodiments of preparations from GOS syrup that are made according to the methods disclosed herein comprise: β-D-Galp-(1→6)-β-D-Galp-(1→6)-β-D-Galp-(1→4)-D-Glcp; β-D-Galp-(1→6)-β-D-Galp-(1→3)-β-D-Galp-(1→4)-D-Glcp; β-D-Galp-(1→6)-β-D-Galp-(1→4)-β-D-Galp-(1→4)-D-Glcp; or any combination thereof. However, such preparations are also essentially free of one or more of: β-D-Galp-(1→4)-[β-D-Galp-(1→6)-]D-Glcp; β-D-Galp-(1→4)-D-Galp; β-D-Galp-(1→2)-[β-D-Galp-(1→4)-]D-Glcp; β-D-Galp-(1→2)-[β-D-Galp-(1→6)-]D-Glcp; β-D-Galp-(1→3)-[β-D-Galp-(1→6)-]D-Glcp; β-D-Galp-(1→4)-β-D-Galp-(1→2)-D-Glcp; β-D-Galp-(1→4)-β-D-Galp-(1→3)-D-Glcp; β-D-Galp-(1→4)-[β-D-Galp-(1→4)-β-D-Galp-(1→6)-]D-Glcp; β-D-Galp-(1→4)-β-D-Galp-(1→4)-β-D-Galp-(1→2)-]D-Glcp; β-D-Galp-(1→4)-β-D-Galp-(1→2)-[β-D-Galp-(1→4)-]D-Glcp; β-D-Galp-(1→4)-β-D-Galp-(1→2)-[β-D-Galp-(1→6)-]D-Glcp; β-D-Galp-(1→4)-β-D-Galp-(1→6)-[β-D-Galp-(1→2)-]D-Glcp; β-D-Galp-(1→4)-β-D-Galp-(1→4)-β-D-Galp-(1→6)-D-Glcp; β-D-Galp-(1→4)-β-D-Galp-(1→4)-β-D-Galp-(1→4)-D-Glcp; β-D-Galp-(1→4)-β-D-Galp-(1→4)-β-D-Galp-(1→2)-D-Glcp; β-D-Galp-(1→4)-β-D-Galp-(1→4)-β-D-Glcp-(1→3)-D-Glcp; β-D-Galp-(1→6)-β-D-Galp-(1→3)-β-D-Galp; β-D-Galp-(1→6)-β-D-Galp-(1→3)-β-D-Glcp-(1→3)-D-Glcp; β-D-Galp-(1→3)-β-D-Galp-(1→6)-D-Glcp; β-D-Galp-(1→3)-β-D-Galp-(1→3)-D-Glcp; β-D-Galp-(1→3)-β-D-Galp-(1→2)-D-Glop; β-D-Galp-(1→3)-β-D-Galp-(1→3)-β-D-Galp-(1→4)-D-Glcp; β-D-Galp-(1→3)-β-D-Galp-(1→3)-β-D-Galp-(1→3)-D-Glcp; β-D-Galp-(1→3)-β-D-Galp-(1→3)-β-D-Galp-(1→2)-D-Glcp; β-D-Galp-(1→3)-β-D-Galp-(1→6)-β-D-Galp-(1→4)-D-Glcp; β-D-Galp-(1→3)-[β-DGalp-(1→6)-]β-D-Galp-(1→4)-D-Glcp; or any combination thereof.

In some embodiments, essentially all trisaccharides in a trisaccharide fraction of the preparation, if present, are linear. Each trisaccharide may terminate with a β-D-Galp-(1→4)-D-Glcp linkage. The trisaccharide fraction may consist essentially of: β-D-Galp-(1→6)-β-D-Galp-(1→4)-D-Glcp; β-D-Galp-(1→3)-β-D-Galp-(1→4)-D-Glcp; β-D-Galp-(1→4)-β-D-Galp-(1→4)-D-Glcp; or any combination thereof.

In some embodiments, the preparation may further include β-D-Galp-(1→3)-D-Galp.

Preparations Containing a Tetrasaccharide Fraction Consisting Essentially of One or Both of β-D-Galp-(1→6)-β-D-Galp-(1→6)-β-D-Galp-(1→4)-D-Glcp and β-D-Galp-(1→6)-β-D-Galp-(1→3)-β-D-Galp-(1→4)-D-Glcp Various embodiments of preparations from GOS syrup that are made according to the methods disclosed herein comprise β-D-Galp-(1→6)-β-D-Galp-(1→6)-β-D-Galp-(1→4)-D-Glcp; β-D-Galp-(1→6)-β-D-Galp-(1→3)-β-D-Galp-(1→4)-D-Glcp, or both, but are essentially free of: β-D-Galp-(1,3)-[β-DGalp-(1→6)-]β-D-Galp-(1→4)-D-Glcp; β-D-Galp-(1→3)-β-D-Galp-(1→6)-β-D-Galp-(1→4)-D-Glcp; β-D-Galp-(1→3)-β-D-Galp-(1→3)-β-D-Galp-(1→4)-D-Glcp; or any combination thereof.

In some embodiments, essentially all trisaccharides in a trisaccharide fraction of the preparation, if present, are linear. Each trisaccharide may terminate with a β-D-Galp-(1→4)-D-Glcp linkage. The trisaccharide fraction may consist essentially of: β-D-Galp-(1→6)-β-D-Galp-(1→4)-D-Glcp; β-D-Galp-(1→3)-β-D-Galp-(1→4)-D-Glcp; β-D-Galp-(1→4)-β-D-Galp-(1→4)-D-Glcp; or any combination thereof.

In some embodiments, the preparation may further include β-D-Galp-(1→3)-D-Galp.

Dietary Supplements and Food Items

GOS syrups or preparations as disclosed herein may be useful in the preparation of dietary supplements, food ingredients, and food items. "Food item" as used herein, is includes beverages and semi-solid food items.

This disclosure further relates to a dietary supplement comprising a GOS syrup or preparation as disclosed herein.

This disclosure further relates to a food item comprising a GOS syrup or a preparation as disclosed herein.

This disclosure further relates to food ingredients comprising a GOS syrup or preparation as disclosed herein.

For example, the GOS syrup may be used in milk and milk products including but not limited to: milk and milk substitutes such as soy milk; milk drinks; yogurt; milk based meal replacements; infant formula; sauces including, but not limited to, white sauces, milk gravies, and chees sauces; milk desserts, including frozen desserts such as ice cream; puddings and custards, including baby foods; and chees soups.

The GOS syrup may also be used in soups including but not limited to: egg soups; soups with legumes as major ingredient; soups with grain products as major ingredient; potato soups; deep-yellow vegetable soups; tomato soups; and other vegetable soups.

The GOS syrup may also be used in nut beverages including, but not limited to, coconut beverages.

The GOS syrup may also be used in bakery products including but not limited to: bread; brownies; cakes, including but not limited to heavy weight cakes, medium weight cakes, light weight cakes, coffee cakes, crumb cakes; pastries including but not limited to doughnuts, Danishes, sweet rolls, toaster pastries; and turnovers; sweet quick type breads; muffins; cookies; cracker; French toast; pancakes; pies; cobblers; fruit crisps; waffles; and grain-based bars with or without filling or coating including but not limited to breakfast bars, granola bars, and rice cereal bars.

The GOS syrup may also be used in cereals including but not limited to: ready-to-eat cereals; ready-to-eat cereals (dry) for baby food; and ready-to-eat cereals (wet) for baby food.

The GOS syrup may also be used in fruit and vegetable juices including but not limited to: fruit juices (including citrus fruit juices) and nectars; vegetable juices; and Fruit juices, vegetable juices and juice mixtures for baby food.

The GOS syrup may also be used non-alcoholic beverages including but not limited to: fruit drinks including but not limited to fruit juice drinks, fruit flavored drinks, and sports drinks; non fruit beverages including energy drinks; and beverage concentrate (powder).

The GOS syrup may also be used in animal feed products.

EXAMPLE 1

An aqueous solution of edible lactose with a starting concentration of 45° Bx as adjusted to pH=5 using hydrochloric acid and equilibrated to 53.5° C. β-D-galactoside galactohydrolase derived from *Aspergillus oryzae* (ENZECO™ Fungal Lactase Concentrate from Enzyme Development Company) was added to the aqueous solution to a concentration of 280 LU per gram of lactose in the aqueous solution. The initial aqueous solution was incubated with the β-D-galactoside galactohydrolase derived from *Aspergillus oryzae* for 195 minutes under constant agitation. Samples of the aqueous solution were taken at 1 min, 2.5 min, 5 min, 10 min, 15 min, 20 min, 25 min, 30 min, 40 min, 50 min, 60, min, 75 min, 90 min, 120 min, and 195 min. The composition of the carbohydrate fractions of the aqueous solution at the different time points are indicated in Table 1.

EXAMPLE 2

4.5 kg of edible lactose was suspended in 5.5 kg of water. The temperature of the suspension was brought to above 90° C. under constant agitation until the lactose was completely dissolved to produce an initial aqueous solution.

The pH of the initial aqueous solution was adjusted to about 4.5 using hydrochloric acid. The temperature of the initial aqueous solution was equilibrated to 55° C. β-D-galactoside galactohydrolase derived from *Aspergillus oryzae* (ENZECO™ Fungal Lactase Concentrate from Enzyme Development Company) was added to the initial aqueous solution to a concentration of 20 LAU/g lactose. The initial aqueous solution was incubated with the β-D-galactoside galactohydrolase derived from *Aspergillus oryzae* for 6 hours under constant agitation. The β-D-galactoside galactohydrolase was then deactivated by adjusting the pH to about 2.0 with HCl.

The resulting intermediate solution comprising of GOS, glucose, galactose, and unreacted lactose, was analyzed by HPLC to ensure that the lactose concentration was reduced to less than 60% of the initial concentration of lactose in the initial aqueous solution (see FIG. 1, Table 2).

The pH of the intermediate solution was adjusted to about pH 8 with 50% KOH. The pH of the intermediate solution was then adjusted to 6.75 with a salt solution comprising of 3.72% w/w citric acid, 6.01% w/w magnesium chloride hexahydrate, and 15.55% w/w dipotassium hydrogen phosphate. β-D-galactoside galactohydrolase derived from *Kluyveromyces lactis* (ENZECO™ Lactase NL 2.5× from Enzyme Development Company) was then added at a dosage of 8.8 LAU/g lactose. The intermediate solution was incubated with β-D-galactoside galactohydrolase derived from *Kluyveromyces lactis* for 10 hours under constant agitation. The β-D-galactoside galactohydrolase derived from *Kluyveromyces lactis* was then deactivated by adjusting the pH to about 3.0 with HCl.

TABLE 1

GOS produced using lactase (280 LU/g lactose) from Aspergillus Oryzae (Enzeco Fungal lactase) at starting lactose of 45 BRIX, T = 53.5 C, pH = 5.

| Time (min) | 1 | 2.5 | 5 | 10 | 15 | 20 | 25 | 30 |
|---|---|---|---|---|---|---|---|---|
| DP5+ | 0.063 | 0.286 | 0.790 | 1.601 | 2.250 | 2.634 | 2.877 | 3.009 |
| DP4 | 1.143 | 2.594 | 4.288 | 5.821 | 6.449 | 6.605 | 6.669 | 6.522 |
| DP3 | 12.532 | 16.610 | 18.862 | 19.508 | 18.954 | 18.265 | 17.792 | 17.223 |
| Lactose | 78.856 | 69.258 | 57.818 | 48.774 | 42.769 | 38.460 | 35.558 | 33.051 |
| DP2 | 0.532 | 0.382 | 2.339 | 2.913 | 4.257 | 5.630 | 6.342 | 7.100 |
| Glucose | 5.881 | 9.039 | 12.695 | 16.687 | 19.316 | 21.209 | 22.778 | 24.148 |
| Galactose | 0.993 | 1.830 | 3.207 | 4.697 | 6.004 | 7.197 | 7.984 | 8.947 |
| TOTAL GOS | 14.271 | 19.872 | 26.280 | 29.843 | 31.910 | 33.134 | 33.680 | 33.854 |

| Time (min) | 40 | 50 | 60 | 75 | 90 | 120 | 195 |
|---|---|---|---|---|---|---|---|
| DP5+ | 3.155 | 3.134 | 3.001 | 2.867 | 2.671 | 2.210 | 1.320 |
| DP4 | 6.299 | 6.051 | 5.649 | 5.247 | 4.917 | 4.214 | 2.957 |
| DP3 | 16.197 | 15.652 | 14.742 | 13.831 | 13.053 | 11.815 | 9.206 |
| Lactose | 28.909 | 26.122 | 23.476 | 20.830 | 18.760 | 15.493 | 10.976 |
| DP2 | 8.657 | 9.674 | 10.650 | 11.626 | 12.136 | 13.289 | 13.673 |
| Glucose | 26.257 | 27.719 | 29.345 | 30.970 | 32.289 | 34.402 | 38.059 |
| Galactose | 10.526 | 11.648 | 13.138 | 14.629 | 16.174 | 18.578 | 23.810 |
| TOTAL GOS | 34.308 | 34.510 | 34.041 | 33.572 | 32.777 | 31.528 | 27.155 |

TABLE 2

% Composition of sugars in GOS mixture following primary transgalactosylation of lactose using fungal β-galactosidase from *Aspergillus oryzae*

| carbohydrate | % w/w of the total carbohydrate |
|---|---|
| DP6 | 0.495 |
| DP5 | 1.884 |
| DP4 | 6.505 |
| DP3 | 19.050 |
| DP2 | 4.005 |
| Lactose | 42.348 |
| Glucose | 19.634 |
| Galactose | 6.079 |
| TOTAL GOS | 31.939 |

Figure 2:
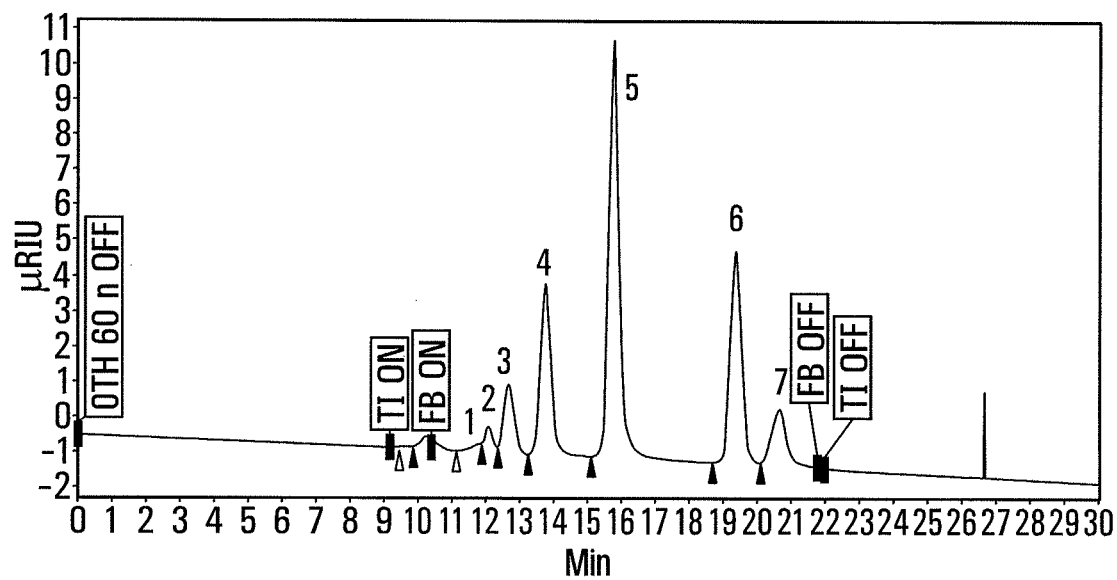
FIG. 2 is a HPLC chromatogram following primary transgalactosylation of lactose using fungal β-D-galactoside galactohydrolases from *Aspergillus oryzae* as disclosed herein in Example 5.
Figure 3:
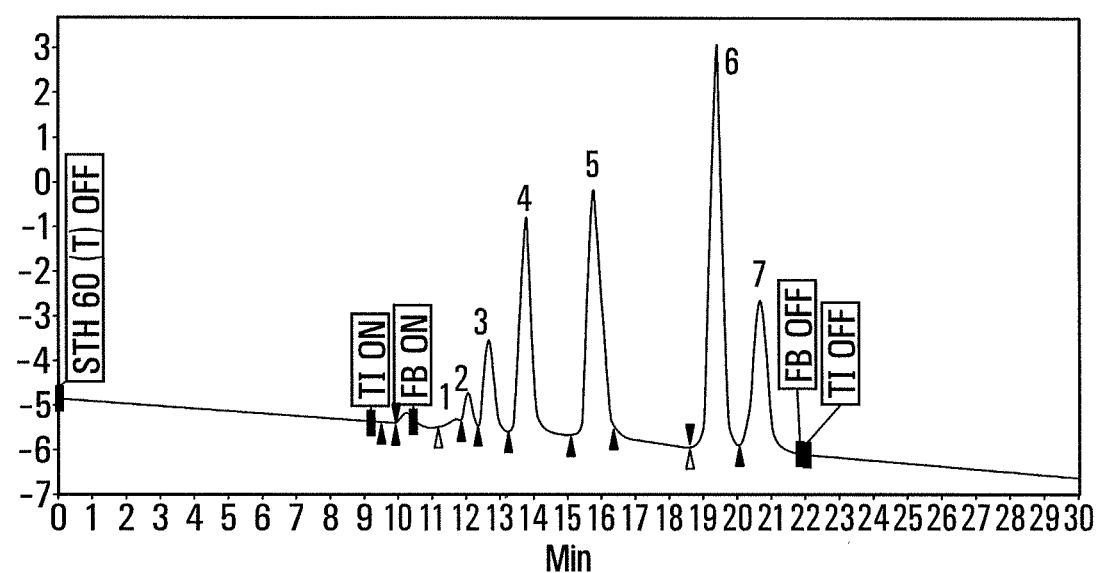
FIG. 3 is a HPLC chromatogram following secondary transgalactosylation of lactose using yeast β-D-galactoside galactohydrolases from *Kluyveromyces* as disclosed herein in Example 5.
Figure 4:
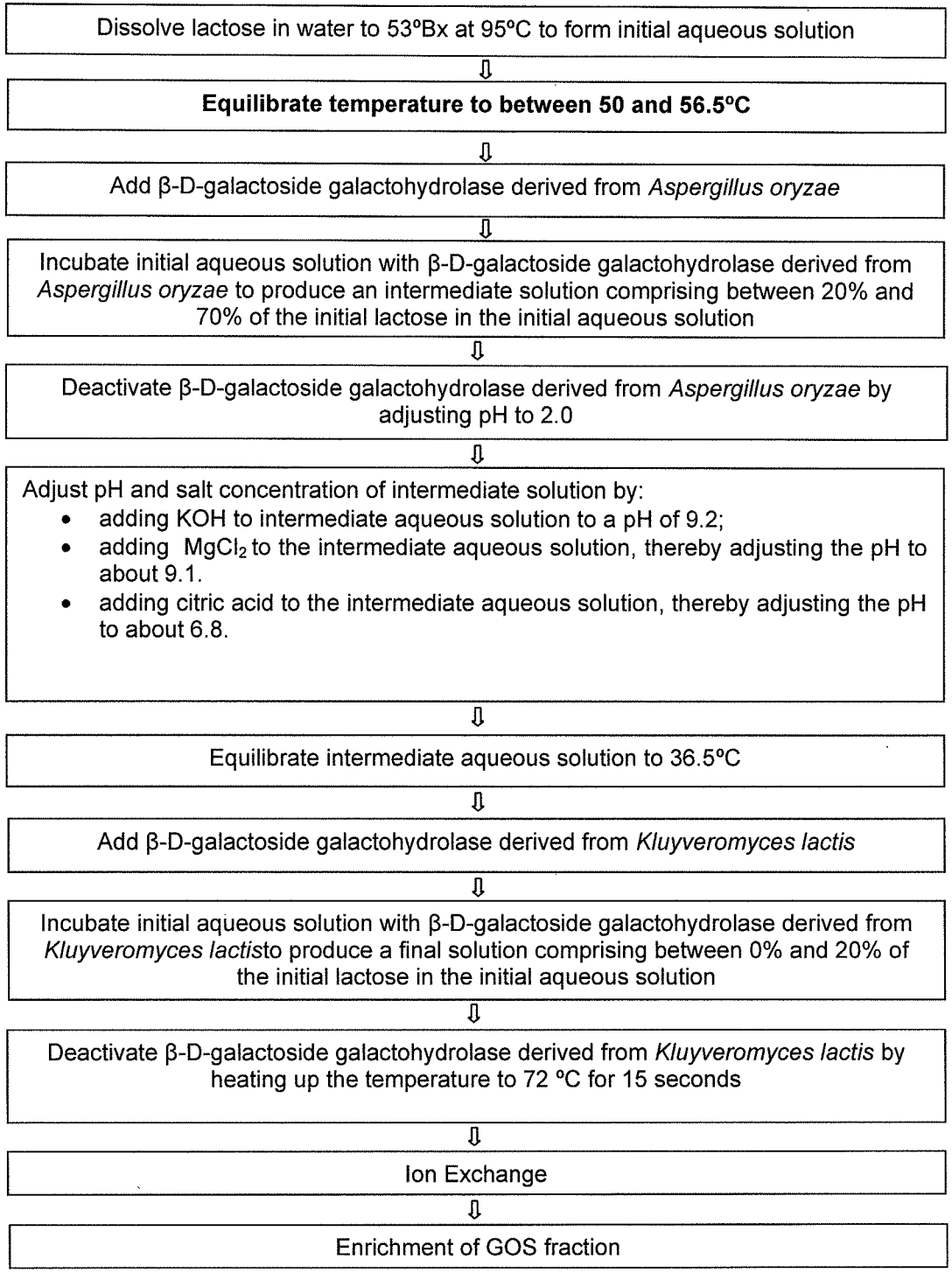
FIG. 4 is a flow diagram of a method of producing GOS syrup as disclosed herein in Example 6.
Figure 5:
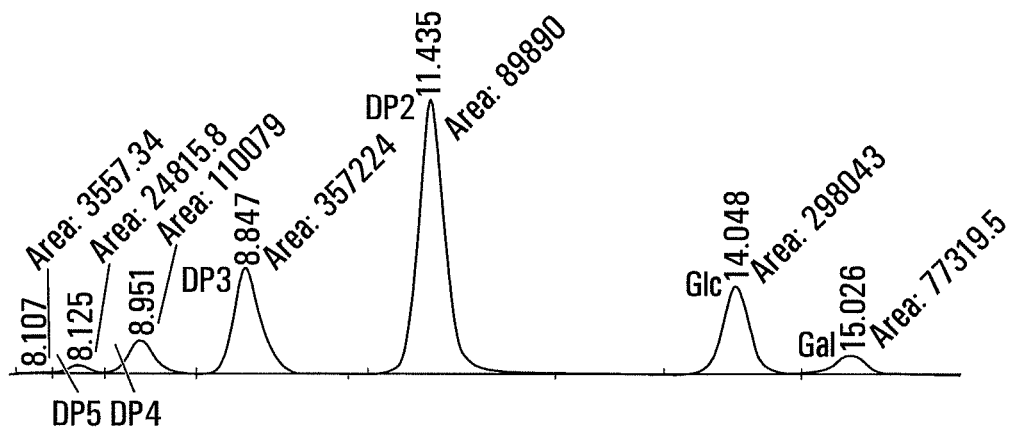
FIG. 5 is a HPLC chromatogram following primary transgalactosylation of lactose using fungal β-D-galactoside galactohydrolases from *Aspergillus oryzae* as disclosed herein in Example 6.
Figure 6:
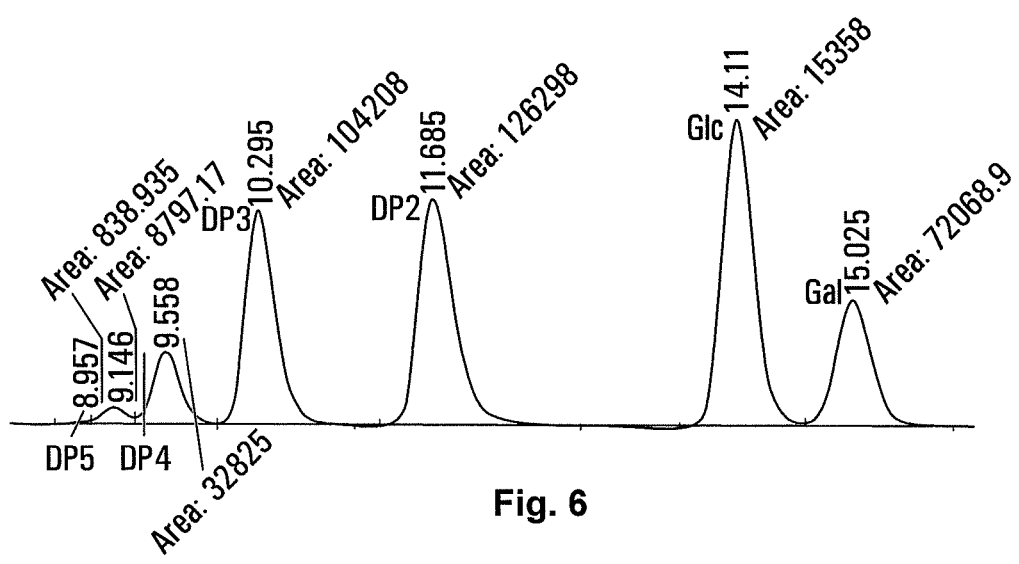
FIG. 6 is a HPLC chromatogram following secondary transgalactosylation of lactose using yeast β-D-galactoside galactohydrolases from *Kluyveromyces* as disclosed herein in Example 6.
Figure 7:
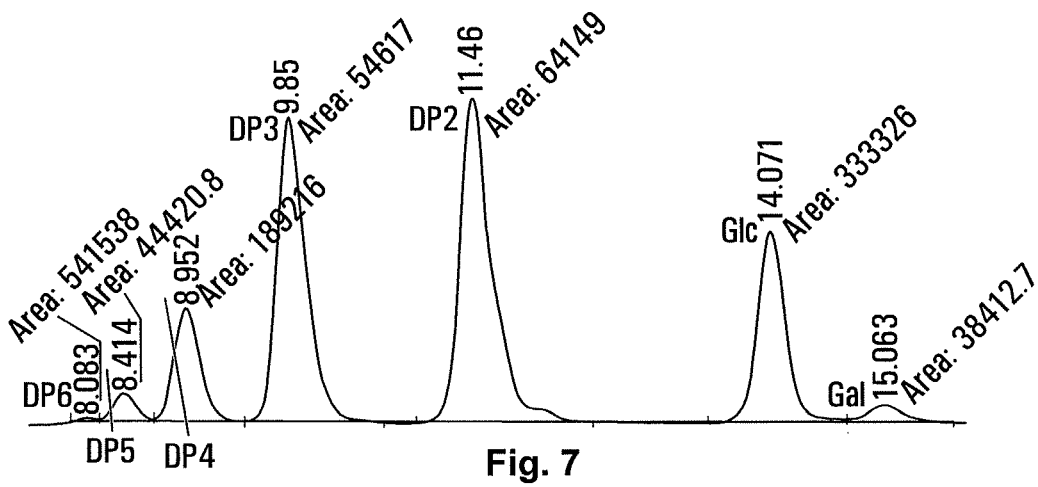
FIG. 7 is a HPLC chromatogram of final product after purification and enrichment as disclosed herein in Example 6.

The resulting final aqueous solution comprising of GOS, glucose, galactose and unreacted lactose, was analyzed by HPLC to ensure that the lactose concentration was to 10% or less than the initial concentration of lactose in the initial solution (see FIG. 2, Table 3).

TABLE 3

% Composition of sugars in GOS mixture following secondary transgalactosylation of lactose using yeast β-galactosidase from *Kluyveromyces*

| carbohydrate | % w/w of the total carbohydrate |
|---|---|
| DP6+ | 0.435 |
| DP5 | 1.908 |
| DP4 | 6.742 |
| DP3 | 18.580 |
| DP2 | 12.842 |
| Lactose | 8.733 |
| Glucose | 33.67 |
| Galactose | 17.082 |
| TOTAL GOS | 40.506 |

EXAMPLE 3

Demineralized, deproteinized, ultrafiltered milk permeate was evaporated to 35 ° Bx, and incubated with β-D-galactoside galactohydrolases derived from *Aspergillus oryzae* and *Kluyveromyces lacti* as described in Example 2. The composition of sugars in the GOS mixture following two-stage transgalactosylation of lactose from ultrafiltered milk permeate is shown in Table 4.

TABLE 4

% Composition of sugars in GOS mixture following two-stage transgalactosylation of lactose from ultrafiltered milk permeate using yeast β-galactosidase from *Aspergillus Oryzae* and *Kluyveromyces Lactis*.

| Name | % w/w of the total carbohydrate |
|---|---|
| DP5+ | 1.328 |
| DP4 | 6.094 |
| DP3 | 18.143 |
| DP2 | 15.475 |
| Lactose | 8.523 |
| Glucose | 33.973 |
| Galactose | 16.464 |
| TOTAL GOS | 41.040 |

EXAMPLE 4

27.4 kg of edible lactose was suspended in 20.8 kg of water to produce a solution of 54° Bx. The temperature of the suspension was brought to above 95° C. under constant agitation until the lactose was completely dissolved to produce an initial aqueous solution. The pH of the initial aqueous solution was 5.4. The temperature of the initial aqueous solution was equilibrated to 58.5° C. β-D-galactoside galactohydrolase derived from *Aspergillus oryzae* (ENZECO™ Fungal Lactase Concentrate from Enzyme Development Company) was added to the initial aqueous solution to a concentration of 277 LU/g lactose. The initial solution was incubated with the β-D-galactoside galactohydrolase derived from *Aspergillus oryzae* for 15 minutes under constant agitation. The β-D-galactoside galactohydrolase was then deactivated by adjusting the pH to about 2.0 with HCl.

The resulting intermediate solution comprising of GOS, glucose, galactose, and unreacted lactose, was analyzed by HPLC to ensure that the lactose concentration was reduced to less than 60% of the initial concentration of lactose in the initial aqueous solution (see Table 5).

The intermediate solution was diluted to 50BRIX. The pH was adjusted to about pH 9.3 with 50% KOH. Magnesium chloride hexahydrate (25 g) was added and the pH adjusted to 6.80 using 50% citric acid. β-D-galactoside galactohydrolase derived from *Kluyveromyces lactis* (ENZECO™ Lactase NL 2.5× from Enzyme Development Company) was then added at a dosage of 40.4 LU/g lactose. The temperature of the solution was adjusted to 40° C. The intermediate solution was incubated with β-D-galactoside galactohydrolase derived from *Kluyveromyces lactis* for 100 minutes under constant agitation. The β-D-galactoside galactohydrolase derived from *Kluyveromyces lactis* was then deactivated by adjusting the pH to about 3.0 with HCl.

TABLE 5

% Composition of sugars in GOS mixture following primary transgalactosylation of lactose using fungal β-galactosidase from *Aspergillus oryzae*

| Name | % w/w of the total carbohydrate |
|---|---|
| DP6 | 0.397 |
| DP5 | 1.812 |
| DP4 | 6.795 |
| DP3 | 19.773 |
| DP2 | 3.216 |
| Lactose | 43.655 |
| Glucose | 18.875 |
| Galactose | 5.478 |
| TOTAL GOS | 31.595 |

The resulting final aqueous solution comprising of GOS, glucose, galactose and unreacted lactose, was analyzed by HPLC (see Table 6).

TABLE 6

% Composition of sugars in GOS mixture following secondary transgalactosylation of lactose using yeast β-galactosidase from *Kluyveromyces*

| Name | % w/w of the total carbohydrate |
|---|---|
| DP6+ | 0.380 |
| DP5 | 1.840 |
| DP4 | 6.892 |

TABLE 6-continued

% Composition of sugars in GOS mixture following secondary transgalactosylation of lactose using yeast β-galactosidase from *Kluyveromyces*

| Name | % w/w of the total carbohydrate |
|---|---|
| DP3 | 19.302 |
| DP2 | 13.403 |
| Lactose | 8.691 |
| Glucose | 32.573 |
| Galactose | 16.919 |
| TOTAL GOS | 41.817 |

EXAMPLE 5

Edible crystalline lactose (Lynn Proteins, Inc., Granton, Wis.) was dissolved in water at 90° C. to a final concentration of 45° Bx to produce an initial aqueous solution of lactose. The temperature of the initial lactose solution was equilibrated to about 53.5° C., and the pH was adjusted to between 4.5 and 5.0 using HCl. Fungal β-D-galactoside galactohydrolase derived from *Aspergillus oryzae* (ENZECO™ Fungal Lactase Concentrate from Enzyme Development Company) was then added to the initial aqueous solution to a concentration of 5.6 LU/g of lactose. The solution was incubated 17 hours under constant agitation to produce an intermediate aqueous solution comprising lactose at a concentration about 40% of the initial concentration of lactose in the initial aqueous solution. The fungal β-D-galactoside galactohydrolase was then deactivated by adjusting the pH to about 2.0 with HCl using a 15% w/w aqueous solution of HCl. After 60 minutes of steady agitation, a 50% w/w solution of KOH was slowly added to the intermediate aqueous solution, thereby adjusting the pH to about 9.30. A 25% w/v solution of magnesium chloride hexahydrate was then added to a concentration of 0.16% w/w of the intermediate aqueous solution, thereby adjusting the pH to about 9.21. Then, a 50% solution of citric acid was slowly added to the intermediate aqueous solution until the pH reached about 6.8. The intermediate aqueous solution was then equilibrated to 36.5° C. Yeast β-D-galactoside galactohydrolase derived from *Kluyveromyces lactis* (ENZECO™ Lactase NL 2.5× from Enzyme Development Company) was then added to a concentration of 4.7 LU/g of lactose to the intermediate aqueous solution. The intermediate aqueous solution was incubated for 17 h under steady agitation to produce a final aqueous solution comprising lactose at a concentration less than 20% of the lactose concentration in the initial aqueous solution. The pH of the final aqueous solution was adjusted to pH 5.5 with citric acid to deactivate the β-D-galactoside galactohydrolase derived from *Kluyveromyces lactis*. The final aqueous solution was then heat treated at 72° C. for 15 seconds. The carbohydrate composition of the final aqueous solution from five trials is provided in Table 7.

The final aqueous solution was subjected to ion exchange purification to remove the salts, lactase enzymes and color components. After ion exchange, the partially purified solution was subjected to a purification step to enrich the GOS fraction. The carbohydrate composition of the GOS syrup final aqueous solution from five trials is provided in Table 7.

TABLE 7

Carbohydrate composition of GOS syrup produced using a combination of lactases from *Aspergillus oryzae* and *Kluyveromyces lactis* prior to chromatographic separation.

| | % w/w of the total carbohydrate | | |
|---|---|---|---|
| Name | Stage 1 (t = 17 h) | Stage 2 (t = 17 h) | Enrichment |
| DP6 | 0.450 | 0.396 | 0.683 |
| DP5 | 1.973 | 1.743 | 2.946 |
| DP4 | 6.743 | 6.638 | 11.133 |
| DP3 | 18.770 | 18.851 | 32.972 |
| DP2 | 4.069 | 12.652 | 18.216 |
| Lactose | 40.792 | 8.830 | 14.891 |
| DP2 + Lactose | 44.861 | 21.482 | 88.107 |
| Glucose | 20.581 | 33.526 | 17.346 |
| Galactose | 6.622 | 17.364 | 1.814 |
| TOTAL GOS | 32.006 | 40.280 | 65.950 |

EXAMPLE 6

Edible crystalline lactose (Lynn Proteins, Inc., Granton, Wis.) was dissolved in water at 95° C. to a final concentration of 53° Bx to produce an initial aqueous solution of lactose. The temperature of the initial lactose solution was equilibrated to about 55-56.5° C., and the pH was adjusted to between 4.5 and 5.5. Fungal β-D-galactoside galactohydrolase derived from *Aspergillus oryzae* (ENZECO™ Fungal Lactase Concentrate from Enzyme Development Company) was then added to the initial aqueous solution to a concentration of 5.8 LU/g of lactose. The solution was incubated 11 hours under constant agitation to produce an intermediate aqueous solution comprising lactose at a concentration about 40% of the initial concentration of lactose in the initial aqueous solution, and DP2 sugar at 49% to 52% of total sugar. Thus, increasing the initial lactose concentration and enzyme concentration reduced the required reaction time from 17 h to 11 h. The fungal β-D-galactoside galactohydrolase was then deactivated by adjusting the pH to about 2.0 with HCl using a 15% w/w aqueous solution of HCl a 20% w/w solution of KOH was slowly added to the intermediate aqueous solution, thereby adjusting the pH to about 9.30. A 25% w/v solution of magnesium chloride hexahydrate was then added to a concentration of 0.16% w/w of the intermediate aqueous solution, thereby adjusting the pH to about 9.21, and essential ions were added to the second enzymatic reaction. Then, a 20% solution of citric acid was slowly added to the intermediate aqueous solution until the pH reached about 6.8. The intermediate aqueous solution was then equilibrated to 36.5° C.

Yeast β-D-galactoside galactohydrolase derived from *Kluyveromyces lactis* (ENZECO™ Lactase NL 2.5× from Enzyme Development Company) was then added to a concentration of 4.4 LU/g of lactose to the intermediate aqueous solution. The intermediate aqueous solution was incubated for 17 h under steady agitation to produce a final aqueous solution comprising lactose at a concentration less than 20% of the lactose concentration in the initial aqueous solution, and DP2 sugar at 23.5% to 25% of total sugar). The final aqueous solution was then heat treated at 72° C. for 15 seconds to deactivate the β-D-galactoside galactohydrolase derived from *Kluyveromyces lactis*. The carbohydrate composition of the final aqueous solution from ten trials is provided in Table 8.

The final aqueous solution was subjected to ion exchange purification to remove the salts, lactase enzymes and color components. After ion exchange, the partially purified solution was subjected to a purification step to enrich the GOS fraction. The carbohydrate composition of the GOS syrup final aqueous solution from five trials is provided in Table 8.

TABLE 8

Carbohydrate composition of GOS syrup produced using a combination of lactases from *Aspergillus oryzae* and *Kluyveromyces lactis* prior to chromatographic separation.

| Name | % w/w of the total carbohydrate | | |
|---|---|---|---|
| | Stage 1 (t = 11 h) | Stage 2 (t = 17 h) | Enrichment |
| DP6 | 0.172 ± 0.051 | 0.187 ± 0.044 | 0.278 ± 0.033 |
| DP5 | 1.407 ± 0.085 | 1.574 ± 0.112 | 2.237 ± 0.136 |
| DP4 | 6.165 ± 0.144 | 6.851 ± 0.254 | 10.126 ± 0.433 |
| DP3 | 19.816 ± 0.691 | 20.042 ± 0.524 | 30.882 ± 0.748 |
| DP2 with lactose | 50.564 ± 0.504 | 23.821 ± 0.783 | 35.460 ± 0.838 |
| Glucose | 17.247 ± 0.553 | 32.108 ± 0.640 | 18.624 ± 0.939 |
| Galactose | 4.623 ± 0.565 | 15.416 ± 0.537 | 2.393 ± 0.607 |
| TOTAL GOS | | | 64.531 ± 1.463 |

EXAMPLE 7

7.1 Methods

The chemical composition and molecular structure of the GOS syrup was further characterized using high performance size exclusion chromatography (HPSEC), high performance anion exchange chromatography (HPAEC), methylation analysis, and 1D & 2D NMR spectroscopy.

Samples were kept at −80° C. overnight and then freeze dried. The percentage of moisture loss was considered as the moisture content.

The oligosaccharide profile in terms of DP value was determined using a high performance size-exclusion chromatograph (HPSEC) equipped with a refractive index detector (RI). A Rezex RSO-01 oligosaccharide $Ag^+$ column was used under temperature of 45° C. The eluent was milli q water containing 0.03% (w/w) $NaN_3$ at a flow rate of 0.2 mL/min. Data analysis was performed using OmniSEC 4.6.1 software.

Monosaccharide composition and oligosaccharide profiles were determined using high performance anion exchange chromatography (HPAEC) with pulsed amperometric detector (PAD). A Dionex system (Dionex, Sunnyvale, Calif.) with a CarboPac PA1 (4 mm 250 mm) and a guard column (3 mm 25 mm) was used. Gradient elution from 150 mM sodium acetate to 150 mM sodium hydroxide with programed flow rate was used. Total monosaccharides composition tests were conducted by treating samples in 1 M sulfuric acid at 100° C. for 2 h in order to achieve complete hydrolysis. Galactose and glucose standards were for calibration. The oligosaccharides profile tests were conducted by directly dissolving samples in water. Samples were then filtered by passing through a 0.45 μm filter before injecting into the column.

For methylation analysis, samples were dissolved in DMSO. Dry sodium hydroxide powder was then added to the solutions under constant stirring at room temperature for 3 h, followed by 2.5 h of constant stirring after adding 0.3 mL methyl iodide. The mixtures were extracted with 1 mL methylene chloride, passed through a sodium sulphate column, and then dried under nitrogen gas. The methylated polysaccharides were then hydrolyzed by adding 0.5 mL 4M trifluoroacetic acid to the sample in a test tube and sealing the tube, heating at 100° C. for 6 h, cooling and then drying with $N_2$. The samples were then dissolved with 0.3 mL distilled water, and the hydrolysates were reduced using 5 mg sodium borodeuteride and acetylated with 0.5 mL acetic anhydride for 2 h. Aliquots of the resultant partially methylated alditol acetates (PMAA) were injected into a GCMS system with ion trap MS detector for analysis.

For NMR spectroscopy, samples were dissolved in $D_2O$ at room temperature with stirring for 2 h, and then freeze dried. This procedure was repeated for three times. Samples were then dissolved in 0.5 mL $D_2O$ for testing. All NMR spectra were obtained on a Bruker 600 MHz NMR spectrometer (Bruker Biospin, Milton, Ontario) with a high-sensitivity $^1H/^{13}C/^{15}N$ cold probe. The sample temperature was regulated to 298 K. Homonuclear $^1H/^1H$ (COSY, TOCSY) and heteronuclear $^1H/^{13}C$ (HSQC and HMBC) spectra were collected using the Bruker-supplied pulse sequences. However, COSY was modified to use a 45 degree final 'read' pulse. A mixing time of 80 ms was used for the TOCSY. COSY and TOCSY spectra were collected with 512 indirect increments spanning 6 ppm, while the HSQC and HMBC spectra were collected with 256 increments spanning 165 ppm and 512 increments spanning 220 ppm, respectively.

For Biogel P-2 Column fractionation, 2 mL samples were diluted 2:1 with Milli-Q water, fractionated on a Bio-Gel P-2 column (90×1 cm), eluted with water at a flow rate of 0.5 mL/min at 22° C. Fractions were screened by phenol-sulfuric assay followed by HPSEC and HPAEC analysis.

7.2 Results

The GOS syrup had a moisture content of 22.9% w/w, which may allow for improved physical stability and shelf life. Monosaccharide composition analysis indicated that it contained 40.3% w/w (dry basis) glucose and 51.1% (w/w, dry basis) galactose.

Figure 8:
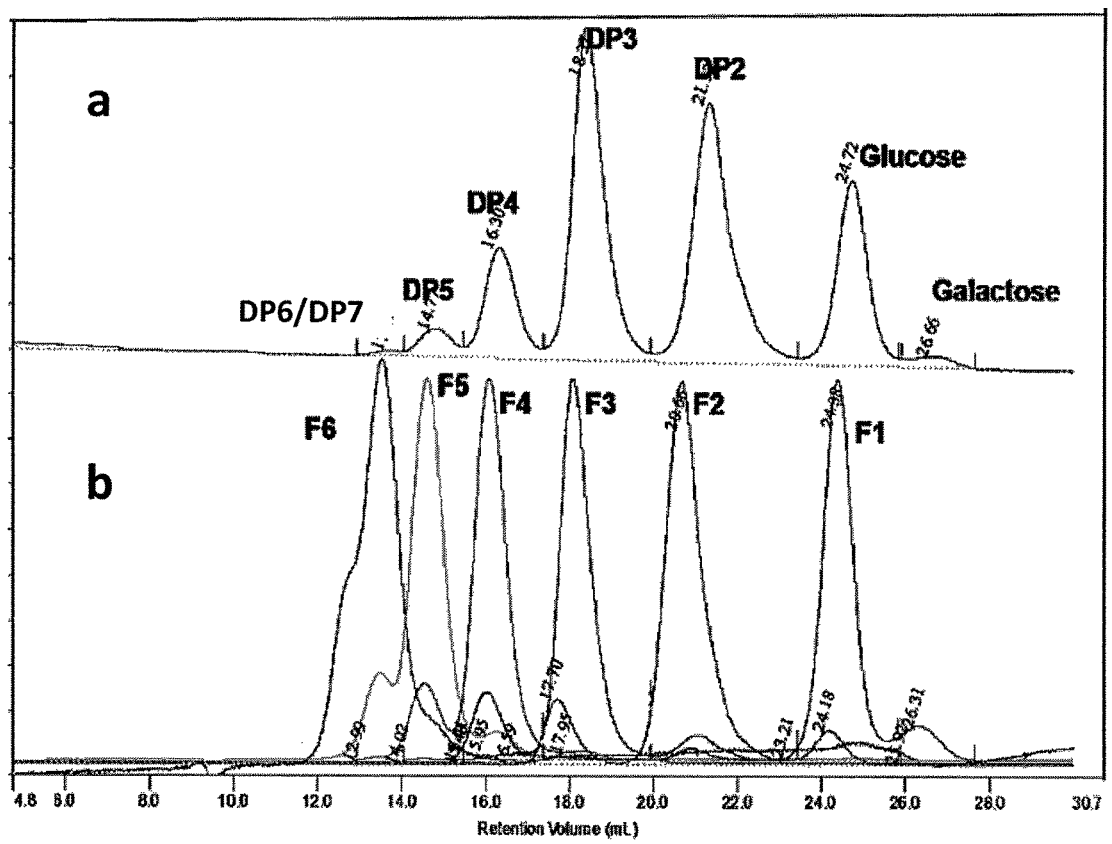
FIG. 8 shows the oligosaccharides profile of (a) GOS syrup produced according to methods disclosed herein and (b) subfractions of the GOS syrup as obtained from HPSEC coupled with RI detector and Rezex RSO-01 oligosaccharide Ag+ column.

FIG. 8A shows the oligosaccharides profile of the GOS syrup as obtained from HPSEC coupled with RI detector and Rezex RSO-01 oligosaccharide $Ag^+$ column. The GOS syrup comprised a mixture of DP1 to DP7. The relative percentages of each DP fraction were 2.1% (galactose), 17.8% (glucose), 32.1% (DP2), 33.5% (DP3), 11.2% (DP4), 2.8% (DP5) and 0.5% (DP6+DP7) based on the percentage of the peak area in FIG. 8a. The free glucose/galactose ratio at the maximum GOS yield, a commonly metric to quantify the ability of different enzymes to catalyze the transgalactosylation reaction (to lactose or galactose acceptors) relative to complete hydrolysis, was 2.1:17.8.

Six sub-fractions (F1 to F6) were collected using the biogel P-2 column. Each was screened using HPSEC (FIG. 8b). Fractions of F1-F6 corresponded to DP1-DP6 enriched fractions, respectively, although a small percentage of mixed components may exist. For example, the F6 fraction contained mainly DP6 species but also small percentage of DP7 species. A small percentage of DP6 species also coexisted with DP5 species in the F5 fraction.

Figure 9:
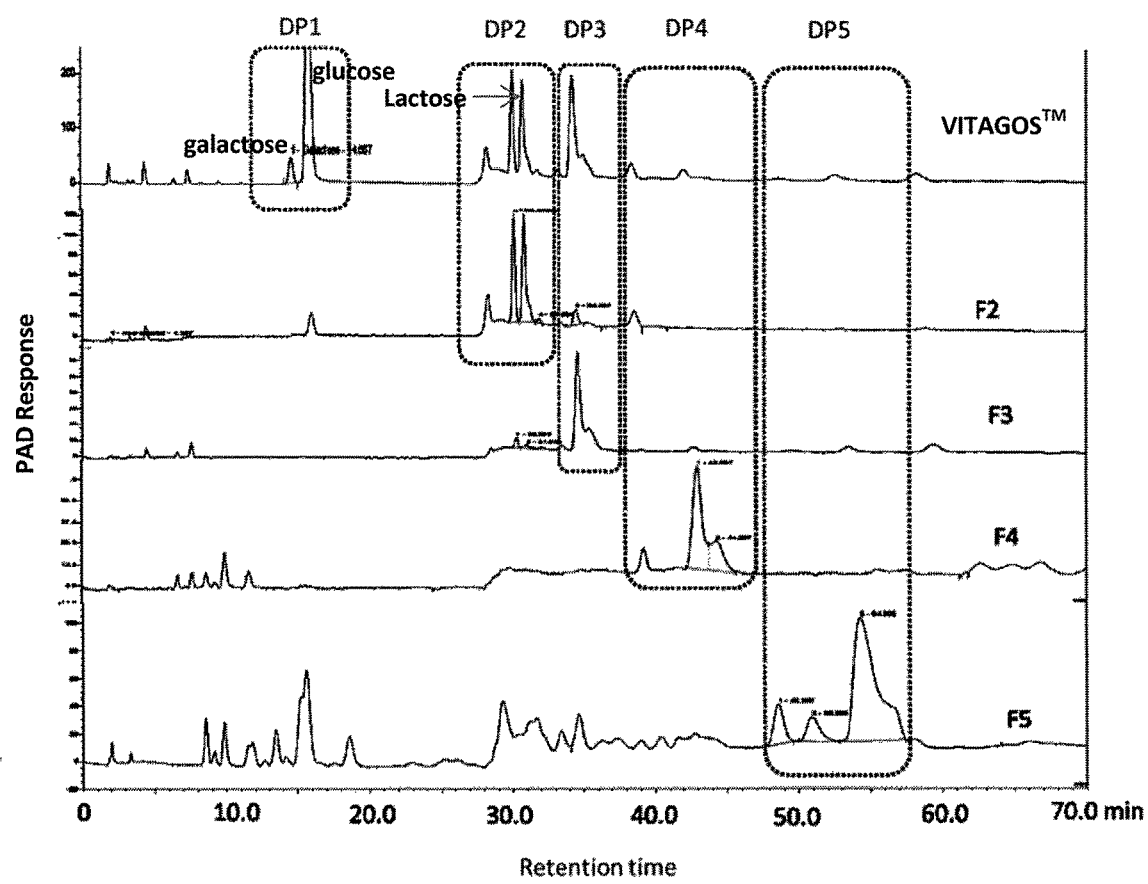
FIG. 9 shows the oligosaccharides profile of GOS syrup produced according to methods disclosed herein and its subfractions as obtained from HPAEC analysis

The oligosaccharides profiles of the GOS syrup and its subfractions were also determined by HPAEC (FIG. 9). FIG. 9 also shows that the GOS syrup is a complex mixture, as more than three species were detected in each DP fraction.

The linkage patterns and relative molar ratios of sugar residues from the GOS syrup and its sub-fractions are summarized in Table 9. The dominant galactose-based sugar residues included T-Galp, 6-GalP, 3-GalP and 4-GalP, the main glucose based sugar residue contained 4-GlcP and T-GlcP. A small percentage of branching sugar residues such as 3,6-GlcP, 2,6-GlcP, 4,6-GlcP, 4,6-GalP, 2,6-GalP, 3,6-GalP were also observed, indicating the existence of trace amounts of branched structures.

For subfractions F2 to F6, the relative percentage of T-GalP and 4-GlcP slightly decreased while that of 3-GalP and 6-GalP increased. The total galactose:glucose ratio increased from 54:46 (F2) to 84:16 (F6) (see Table 10). The 6-linked glycosidic bond was favored by the transgalactosylation reaction of the enzymes used.

TABLE 9

Linkage patterns of sugar residues from GOS syrup and its subfractions

| Linkage types | GOS syrup (mol %) | F2[a] (mol %) | F3[a] (mol %) | F4[a] (mol %) | F5[a] (mol %) | F6[a] (mol %) |
|---|---|---|---|---|---|---|
| 4-GlcP | 13.9% | 17.9% | 26.7% | 23.6% | 18.2% | 16.1% |
| 6-GlcP | 1.4% | 14.9% | 2.5% | —[b] | — | — |
| T-GlcP | 7.3% | 5.4% | — | — | — | — |
| 3-GlcP | 1.0% | 4.9% | — | — | — | — |
| 2-GlcP | 1.5% | 2.4% | — | — | — | — |
| Total GGlcP | 25.1% | 45.5% | 29.2% | 23.6% | 18.2% | 16.1% |
| T-GalP | 44.7% | 43.9% | 33.5% | 31.% | 28.4% | 25.2% |
| 6-GalP | 18.8% | 5.6% | 23.5% | 32.5% | 36.6% | 39.4% |
| 3-GalP | 7.8% | 4.9% | 9.3% | 8.0% | 10.2% | 12.1% |
| 4-GalP | 3.6% | — | 4.4% | 4.8% | 6.6% | 7.3% |
| Total GalP | 74.9% | 54.4% | 70.7% | 76.3% | 81.8% | 84.0% |

Figure 10:
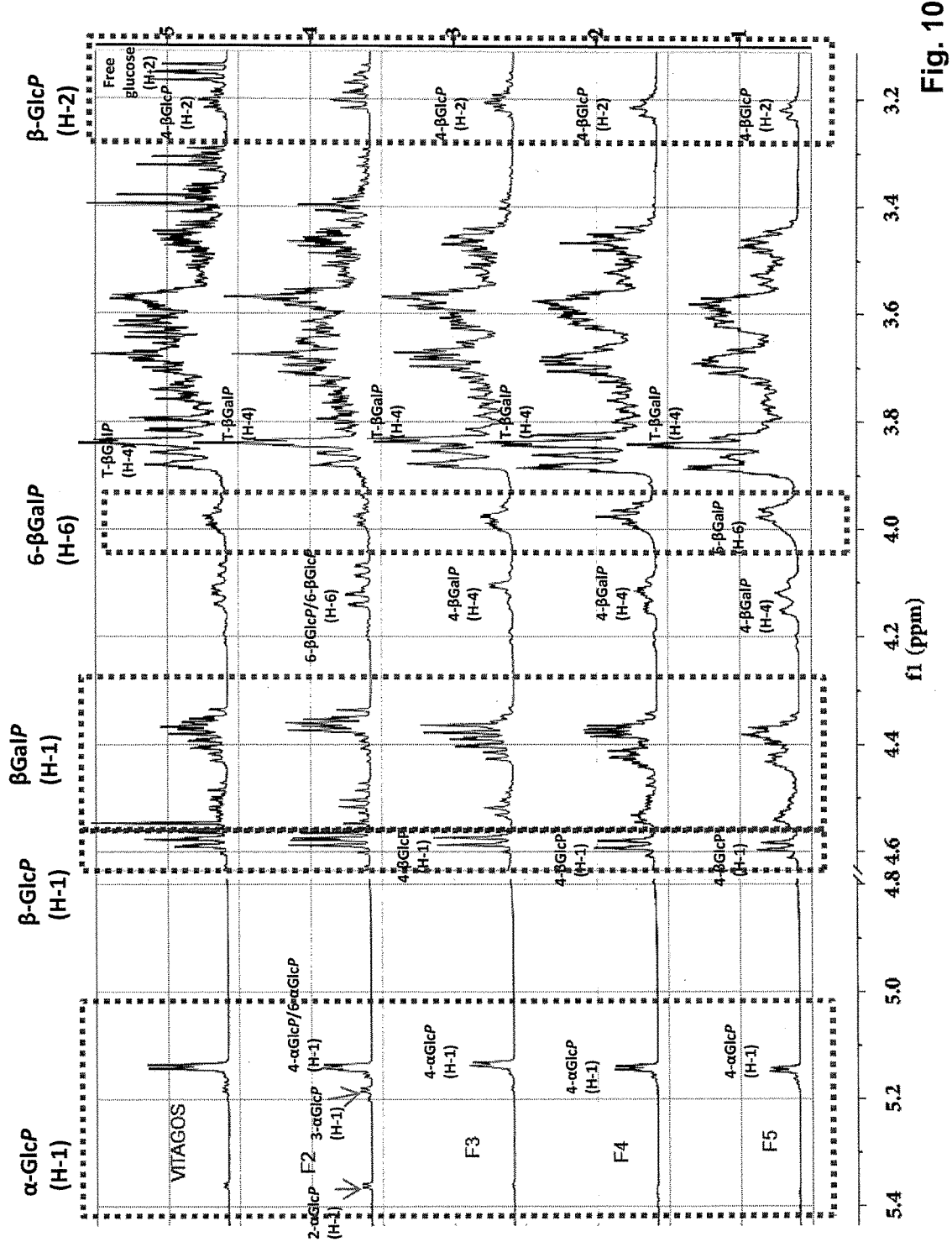
FIG. 10 is $^1$H NMR spectra of GOS syrup produced according to methods disclosed herein and its subfractions (F2-F5)
Figure 11:
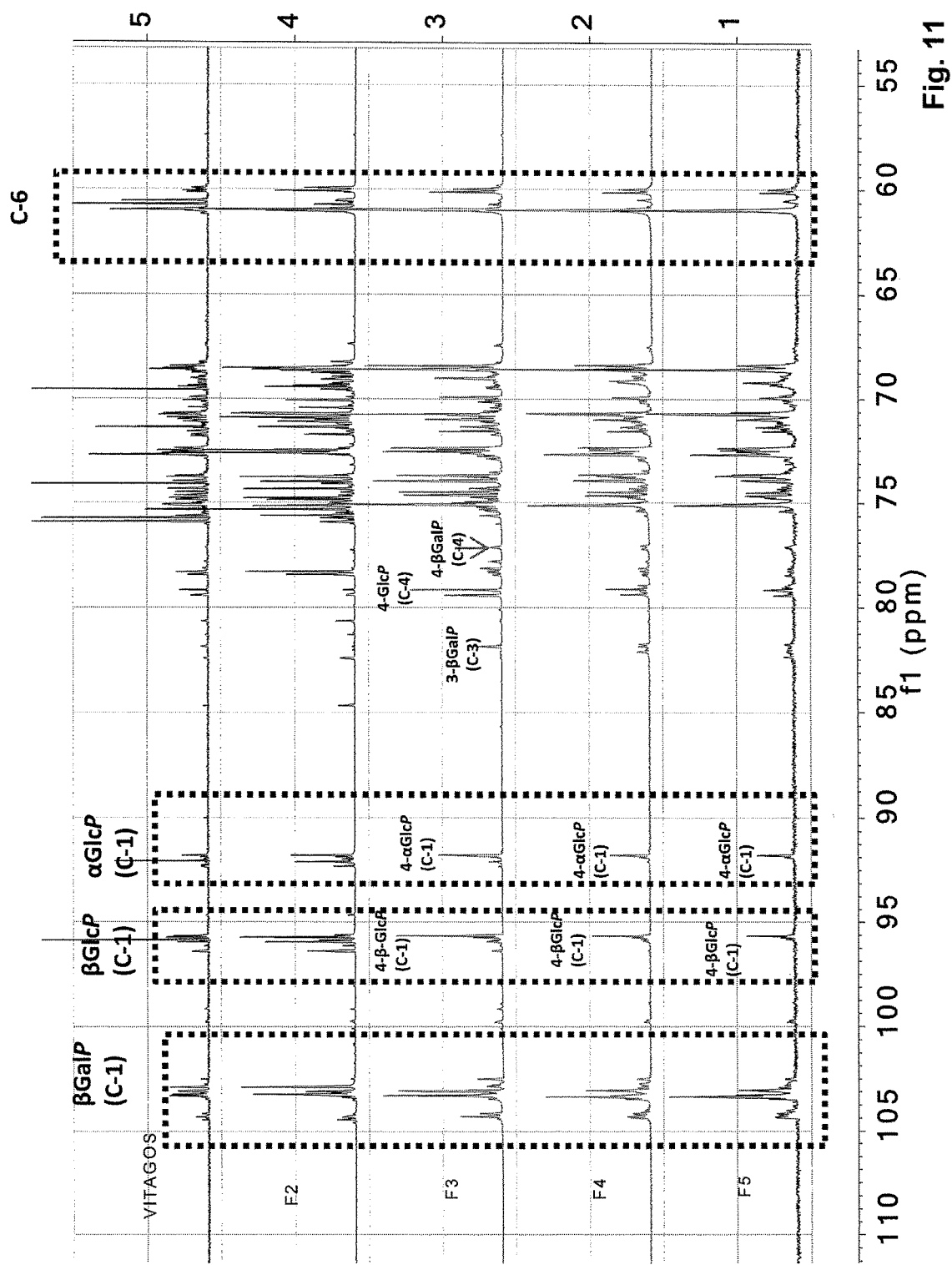
FIG. 11 is $^{13}$C NMR spectra of GOS syrup produced according to methods disclosed herein and its subfractions (F2-F5)

From FIG. 10 and FIG. 11, it may be observed that most of the galactose-based sugar residues (T-GalP, 3-GalP, 4-GalP and 6-GalP) were in β-configuration, whereas glucose-based sugar residues (4-GlcP) were in both α- and β-configurations. T-βGalP was generally found in the non-reducing end of the molecules while 4-GlcP was generally found in the reducing end except for F2 fraction. Third, the ratio of total Gal:Glc derived from the peak integration of $^1$H spectra (FIG. 10) were 51.4:48.6 (GOS syrup), 54.8:45.2 (F2), 67.4:32.6 (F3), 78.3:21.7 (F4) and 78.6:21.4 (F5), which is consistent with the results obtained from monosaccharides composition and methylation analysis (Table 10).

2D NMR spectroscopy, including homonuclear correlation spectrum (COSY), total correlated spectroscopy (TOCSY, heteronuclear multiple-quantum coherence spectroscopy (HSQC) and heteronuclear multiple bond correlation spectroscopy (HMBC), was also included in the study. COSY and TOCSY can help to identify the complete proton chemical shift. HSQC is used to establish the correlation between proton and $^{13}$C. HMBC is used to identify the sequences of different sugar residues.

TABLE 10

Total sugar composition of the GOS syrup

| Saccharide (DP) | Structure | Relative percentage of each sugar fraction in each DP pool (%)[a] | Total weight percentage (%)[b] |
|---|---|---|---|
| DP1 | Galactose | 10.6 | 19.9 |
| | Glucose | 89.4 | |
| DP2 | βGal(1→4)Glc (lactose) | 34.2 | 32.1 |
| | βGal(1→6)Glc[a] | 30.5 | |
| | βGal(1→6)Gal | 11.1 | |
| | βGal(1→3)Glc | 9.7 | |
| | βGal(1→3)Gal | 9.7 | |
| | βGal(1→2)Glc | 4.7 | |
| | Other | Trace amount | |
| DP3 | βGal(1→6)βGal(1→4)Glc[a] | 63.2 | 33.5 |
| | βGal(1→3)βGal(1→4)Glc | 25.0 | |
| | βGal(1→4)βGal(1→4)Glc | 11.8 | |
| | Others | Trace amount | |
| DP4 | βGal(1→6)βGal(1→6)βGal(1→4)Glc[a] | 40.9 | 11.2 |
| | βGal(1→6)βGal(1→3)βGal(1→4)Glc | 37.0 | |
| | βGal(1→6)βGal(1→4)βGal(1→4)Glc | 22.2 | |
| | others | Trace amount | |
| DP5 | Not obtained | — | 2.8 |
| DP6 + DP7 | Not obtained | — | 0.5 |

[a]obtained from the results of methylation analysis and confirmed by peak integration of $^1$H NMR spectroscopy
[b]deduced from HPSEC analysis based on relative peak area The structural information obtained from methylation analysis and 1D&2D NMR spectroscopy is summarized in Table 10. For the F2 fraction (DP2), the dominant terminal sugar residue was T-GalP (45.5%) with a small percentage of T-GlcP (5.4%), while the sugar residues residing on the reducing end included 4-GlcP (17.9%), 6-GlcP (14.9%), β-GalP (5.6%), 3-GlcP (4.9%), 2-GlcP (2.4%). Five disaccharides were confirmed in F2 fraction, including βGal (1→4)Glc (lactose), βGal (1→6)-Glc, βGal (1→6)Gal, βGal (1→3)Glc, βGal (1→3)Gal, and βGal (1→2)Gal. A small percentage of T-GlcP based disaccharides such as GlcP (1→4) Glc may also exist in the F2 fraction in low abundance.

Figure 12:
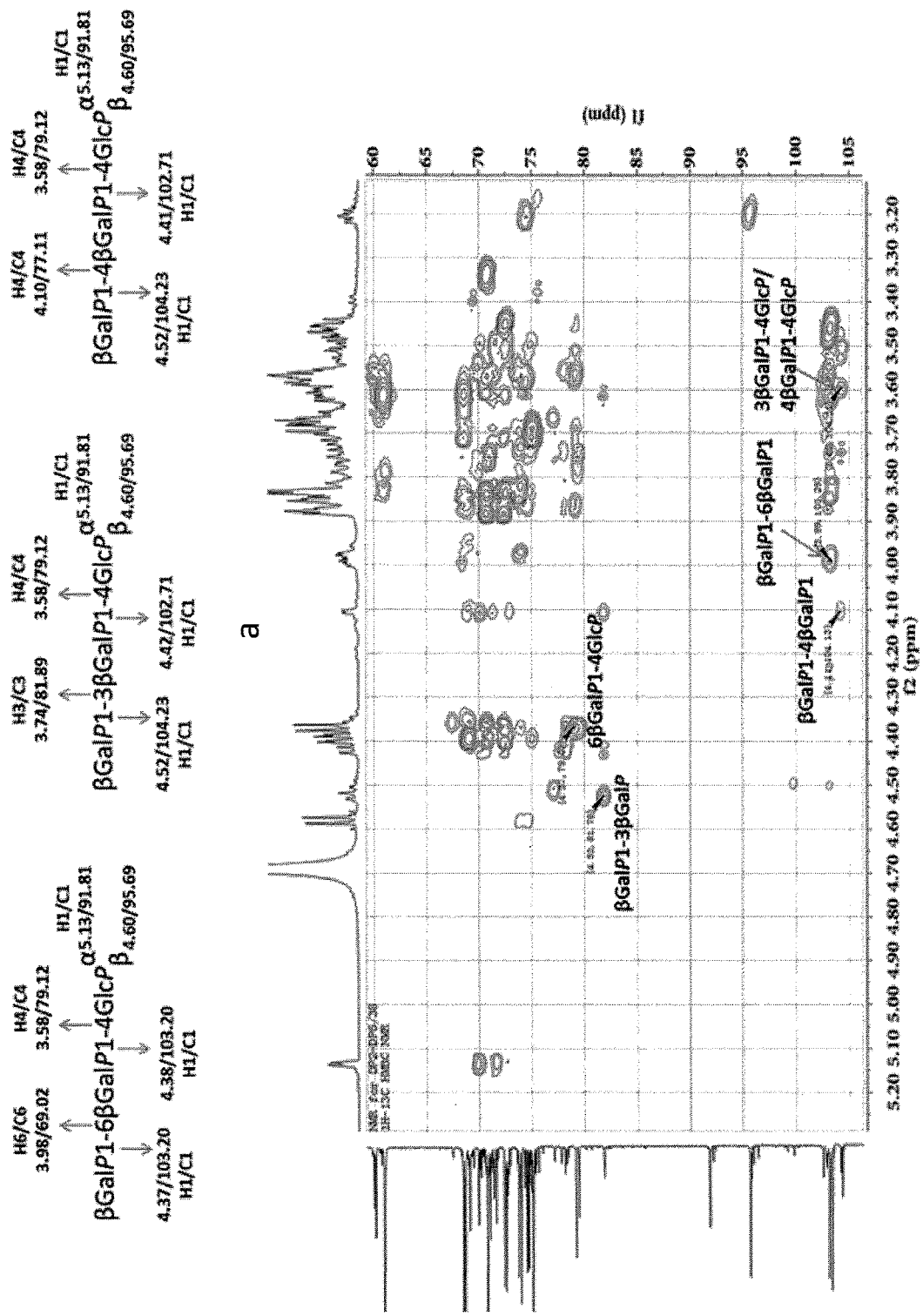
FIG. 12 shows (a) the three tri-saccharides in GOS syrup produced according to methods disclosed herein and (b) their observed connectivities in HMBC spectrum.

For the F3 fraction, the dominant terminal sugar residue (non-reducing end) and dominant reducing end sugar residue were T-GalP (29.2%) and 4-GlcP (26.7%), respectively. Compared to F2, sugar residues including 6-GalP (23.5%), 3-GalP (9.3%) and 4-GalP (4.4%) were enriched. This indicates that the following three tri-saccharides are present in this fraction: GalP-β (1→6)GalP-β (1→4)Glc (dominant peak), GalP-β (1→3)GalP-β (1→4)Glc, and GalP-β (1→4)GalP-β (1→4)Glc. All the three fractions have been evidenced in 1D and 2D NMR spectrum. All the connections demonstrated by HMBC spectroscopy are presented in FIG. 12. Notably, each of the trisaccharides in the trisaccharide fraction are linear, and each terminates with a β-D-Galp-(1→4)-D-Glcp linkage.

The F4 fraction included similar sugar residues to F3. However, 6-GalP was significantly enriched, while T-GalP and 4-GlcP were lower (Table 9). In addition, similar $^1$H and $^{13}$C spectrum in the F4 and F3 fractions suggested similar structural features among them. According to 1D and 2D NMR spectrum, the F4 fraction includes at least the following three molecular structures: βGal(1→6)βGal(1→6)βGal(1→4)Glc, βGal(1→6)βGal(1→3)βGal(1→4)Glc, and βGal(1→6)βGal(1→4)βGal(1→4)Glc. The dominant fraction as shown in FIG. 9 was assigned to βGal(1→6)βGal(1→6)βGal(1→4)Glc. Notably, each of these tetrasaccharides has at least one β-D-Galp-(1→6)-linkage.

The F5 and F6 fractions showed similar dominant sugar residues, namely T-GalP (26.7% and 23.4%), 6-GalP (29.7% and 29.6%), 4-GlcP (13.9% and 11.5%), and 3-GalP (9.6% and 11.2%).

While specific embodiments of the invention have been described and illustrated, such embodiments should be considered illustrative of the invention only and not as limiting the invention as construed in accordance with the accompanying claims.

What is claimed is:

1. A galactooligosaccharide (GOS) composition comprising:
   galactose;
   glucose;
   β-D-Galp-(1→3)-D-Galp;
   β-D-Galp-(1→6)-D-Galp;
   β-D-Galp-(1→3)-D-Glcp;
   β-D-Galp-(1→4)-D-Glcp;
   β-D-Galp-(1→6)-β-D-Galp-(1→4)-D-Glcp;
   β-D-Galp-(1→2)-D-Glcp;
   β-D-Galp-(1→3)-DGlcp;
   β-D-Galp-(1→4)-β-D-Galp-(1→4)-D-Glcp;
   β-D-Galp-(1→3)-β-D-Galp-(1→4)-D-Glcp;
   β-D-Galp-(1→6)-β-D-Galp-(1→6)-β-D-Galp-(1→4)-D-Glcp;
   β-D-Galp-(1→6)-β-D-Galp-(1→3)-β-D-Galp-(1→4)-D-Glcp; and
   β-D-Galp-(1→6)-β-D-Galp-(1→4)-β-D-Galp-(1→4)-D-Glcp.

2. A dietary supplement comprising a galactooligosaccharide (GOS) composition as defined in claim 1.

3. A food item comprising a galactooligosaccharide (GOS) composition as defined in claim 1.

4. The GOS composition of claim 1, wherein the GOS composition is essentially free of one or more of:
   β-D-Galp-(1→4)-[β-D-Galp-(1→6)-]D-Glcp;
   β-D-Galp-(1→4)-D-Galp;
   β-D-Galp-(1→2)-[β-D-Galp-(1→4)-]D-Glcp;
   β-D-Galp-(1→2)-[β-D-Galp-(1→6)-]D-Glcp;
   β-D-Galp-(1→3)-[β-D-Galp-(1→6)-]D-Glcp;
   β-D-Galp-(1→4)-β-D-Galp-(1→2)-D-Glcp;
   β-D-Galp-(1→4)-β-D-Galp-(1→3)-D-Glcp;
   β-D-Galp-(1→4)-[β-D-Galp-(1→4)-β-D-Galp-(1→6)-]D-Glcp;
   β-D-Galp-(1→4)-β-D-Galp-(1→4)-[β-D-Galp-(1→6)-]D-Glcp;
   β-D-Galp-(1→4)-β-D-Galp-(1→4)-[β-D-Galp-(1→2)-]D-Glcp;
   β-D-Galp-(1→4)-β-D-Galp-(1→2)-[β-D-Galp-(1→4)-]D-Glcp;
   β-D-Galp-(1→4)-β-D-Galp-(1→2)-[β-D-Galp-(1→6)-]D-Glcp;
   β-D-Galp-(1→4)-β-D-Galp-(1→6)-[β-D-Galp-(1→2)-]D-Glcp;
   β-D-Galp-(1→4)-β-D-Galp-(1→4)-β-D-Galp-(1→6)-D-Glcp;
   β-D-Galp-(1→4)-β-D-Galp-(1→4)-β-D-Galp-(1→4)-D-Glcp;
   β-D-Galp-(1→4)-β-D-Galp-(1→4)-β-D-Galp-(1→2)-D-Glcp;
   β-D-Galp-(1→4)-β-D-Galp-(1→4)-β-D-Galp-(1→3)-D-Glcp;
   β-D-Galp-(1→6)-β-D-Galp-(1→3)-D-Glcp;
   β-D-Galp-(1→6)-β-D-Galp-(1→4)-β-D-Galp-(1→3)-D-Glcp;
   β-D-Galp-(1→3)-β-D-Galp-(1→6)-D-Glcp;
   β-D-Galp-(1→3)-β-D-Galp-(1→3)-D-Glcp;
   β-D-Galp-(1→3)-β-D-Galp-(1→2)-D-Glcp;
   β-D-Galp-(1→3)-β-D-Galp-(1→3)-β-D-Galp-(1→4)-D-Glcp;
   β-D-Galp-(1→3)-β-D-Galp-(1→3)-β-D-Galp-(1→3)-D-Glcp;
   β-D-Galp-(1→3)-β-D-Galp-(1→3)-β-D-Galp-(1→2)-D-Glcp;
   β-D-Galp-(1→3)-β-D-Galp-(1→6)-β-D-Galp-(1→4)-D-Glcp; and
   β-D-Galp-(1→3)-[β-DGalp-(1→6)-]β-D-Galp-(1→4)-D-Glcp.

5. The GOS composition of claim 1, wherein essentially all tetrasaccharides in a tetrasaccharide fraction of the GOS composition include a β-D-Galp-(1→6)- linkage.

6. The GOS composition of claim 1, wherein a tetrasaccharide fraction of the GOS composition consists essentially of:
   β-D-Galp-(1→6)-β-D-Galp-(1→6)-β-D-Galp-(1→4)-D-Glcp;
   β-D-Galp-(1→6)-β-D-Galp-(1→3)-β-D-Galp-(1→4)-D-Glcp; and
   β-D-Galp-(1→6)-β-D-Galp-(1→4)-β-D-Galp-(1→4)-D-Glcp.

7. The GOS composition of claim 4, wherein essentially all tetrasaccharides in a tetrasaccharide fraction of the GOS composition include a β-D-Galp-(1→6)- linkage.

8. The GOS composition of claim 1, wherein essentially all trisaccharides in a trisaccharide fraction of the GOS composition are linear.

9. The GOS composition of claim 1, wherein a trisaccharide fraction of the GOS composition consists essentially of:
β-D-Galp-(1→6)-β-D-Galp-(1→4)-D-Glcp;
β-D-Galp-(1→3)-β-D-Galp-(1→4)-D-Glcp; and
β-D-Galp-(1→4)-β-D-Galp-(1→4)-D-Glcp.

10. The GOS composition of claim 8, wherein each trisaccharide in the trisaccharide fraction terminates with a β-D-Galp-(1→4)-D-Glcp linkage.

11. The GOS composition of claim 4, wherein each trisaccharide in a trisaccharide fraction of the GOS composition terminates with a β-D-Galp-(1→4)-D-Glcp linkage.

12. The GOS composition of claim 1, wherein each trisaccharide in a trisaccharide fraction of the GOS composition terminates with a β-D-Galp-(1→4)-D-Glcp linkage.

13. The GOS composition of claim 4, wherein a trisaccharide fraction of the GOS composition consists essentially of:
β-D-Galp-(1→6)-β-D-Galp-(1→4)-D-Glcp;
β-D-Galp-(1→3)-β-D-Galp-(1→4)-D-Glcp; and
β-D-Galp-(1→4)-β-D-Galp-(1→4)-D-Glcp.

14. The GOS composition of claim 5, wherein each trisaccharide in a trisaccharide fraction of the GOS composition terminates with a β-D-Galp-(1→4)-D-Glcp linkage.

15. The GOS composition of claim 6, wherein each trisaccharide in a trisaccharide fraction of the GOS composition terminates with a β-D-Galp-(1→4)-D-Glcp linkage.

16. The GOS composition of claim 5, wherein a trisaccharide fraction of the GOS composition consists essentially of:
β-D-Galp-(1→6)-β-D-Galp-(1→4)-D-Glcp;
β-D-Galp-(1→3)-β-D-Galp-(1→4)-D-Glcp; and
β-D-Galp-(1→4)-β-D-Galp-(1→4)-D-Glcp.

17. The GOS composition of claim 6, wherein a trisaccharide fraction of the GOS composition consists essentially of:
β-D-Galp-(1→6)-β-D-Galp-(1→4)-D-Glcp;
β-D-Galp-(1→3)-β-D-Galp-(1→4)-D-Glcp; and
β-D-Galp-(1→4)-β-D-Galp-(1→4)-D-Glcp.

18. The GOS composition of claim 5, wherein essentially all trisaccharides in a trisaccharide fraction of the GOS composition are linear.

19. The GOS composition of claim 18, wherein each trisaccharide in the trisaccharide fraction of the GOS composition terminates with a β-D-Galp-(1→4)-D-Glcp linkage.

20. The GOS composition of claim 6, wherein essentially all trisaccharides in a trisaccharide fraction of the GOS composition are linear.

21. The GOS composition of claim 20, wherein each trisaccharide in the trisaccharide fraction of the GOS composition terminates with a β-D-Galp-(1→4)-D-Glcp linkage.

22. The GOS composition of claim 5, wherein the GOS composition is essentially free of one or more of:
β-D-Galp-(1→4)-[β-D-Galp-(1→6)-]D-Glcp;
β-D-Galp-(1→4)-D-Galp;
β-D-Galp-(1→2)-[β-D-Galp-(1→4)-]D-Glcp;
β-D-Galp-(1→2)-[β-D-Galp-(1→6)-]D-Glcp;
β-D-Galp-(1→3)-[β-D-Galp-(1→6)-]D-Glcp;
β-D-Galp-(1→4)-β-D-Galp-(1→2)-D-Glcp;
β-D-Galp-(1→4)-β-D-Galp-(1→3)-D-Glcp;
β-D-Galp-(1→4)-[β-D-Galp-(1→4)-β-D-Galp-(1→6)-]D-Glcp;
β-D-Galp-(1→4)-β-D-Galp-(1→4)-[β-D-Galp-(1→6)-]D-Glcp;
β-D-Galp-(1→4)-β-D-Galp-(1→4)-[β-D-Galp-(1→2)-]D-Glcp;
β-D-Galp-(1→4)-β-D-Galp-(1→2)-[β-D-Galp-(1→4)-]D-Glcp;
β-D-Galp-(1→4)-β-D-Galp-(1→2)-[β-D-Galp-(1→6)-]D-Glcp;
β-D-Galp-(1→4)-β-D-Galp-(1→6)-[β-D-Galp-(1→2)-]D-Glcp;
β-D-Galp-(1→4)-β-D-Galp-(1→4)-β-D-Galp-(1→6)-D-Glcp;
β-D-Galp-(1→4)-β-D-Galp-(1→4)-β-D-Galp-(1→4)-D-Glcp;
β-D-Galp-(1→4)-β-D-Galp-(1→4)-β-D-Galp-(1→2)-D-Glcp;
β-D-Galp-(1→4)-β-D-Galp-(1→4)-β-D-Galp-(1→3)-D-Glcp;
β-D-Galp-(1→6)-β-D-Galp-(1→3)-D-Glcp;
β-D-Galp-(1→6)-β-D-Galp-(1→4)-β-D-Galp-(1→3)-D-Glcp;
β-D-Galp-(1→3)-β-D-Galp-(1→6)-D-Glcp;
β-D-Galp-(1→3)-β-D-Galp-(1→3)-D-Glcp;
β-D-Galp-(1→3)-β-D-Galp-(1→2)-D-Glcp;
β-D-Galp-(1→3)-β-D-Galp-(1→3)-β-D-Galp-(1→4)-D-Glcp;
β-D-Galp-(1→3)-β-D-Galp-(1→3)-β-D-Galp-(1→3)-D-Glcp;
β-D-Galp-(1→3)-β-D-Galp-(1→3)-β-D-Galp-(1→2)-D-Glcp;
β-D-Galp-(1→3)-β-D-Galp-(1→6)-β-D-Galp-(1→4)-D-Glcp; and
β-D-Galp-(1→3)-[β-DGalp-(1→6)-]β-D-Galp-(1→4)-D-Glcp.

23. The GOS composition of claim 6, wherein the GOS composition is essentially free of one or more of:
β-D-Galp-(1→4)-[β-D-Galp-(1→6)-]D-Glcp;
β-D-Galp-(1→4)-D-Galp;
β-D-Galp-(1→2)-[β-D-Galp-(1→4)-]D-Glcp;
β-D-Galp-(1→2)-[β-D-Galp-(1→6)-]D-Glcp;
β-D-Galp-(1→3)-[β-D-Galp-(1→6)-]D-Glcp;
β-D-Galp-(1→4)-β-D-Galp-(1→2)-D-Glcp;
β-D-Galp-(1→4)-β-D-Galp-(1→3)-D-Glcp;
β-D-Galp-(1→4)-[β-D-Galp-(1→4)-β-D-Galp-(1→6)-]D-Glcp;
β-D-Galp-(1→4)-β-D-Galp-(1→4)-[β-D-Galp-(1→6)-]D-Glcp;
β-D-Galp-(1→4)-β-D-Galp-(1→4)-[β-D-Galp-(1→2)-]D-Glcp;
β-D-Galp-(1→4)-β-D-Galp-(1→2)-[β-D-Galp-(1→4)-]D-Glcp;
β-D-Galp-(1→4)-β-D-Galp-(1→2)-[β-D-Galp-(1→6)-]D-Glcp;
β-D-Galp-(1→4)-β-D-Galp-(1→6)-[β-D-Galp-(1→2)-]D-Glcp;
β-D-Galp-(1→4)-β-D-Galp-(1→4)-β-D-Galp-(1→6)-D-Glcp;
β-D-Galp-(1→4)-β-D-Galp-(1→4)-β-D-Galp-(1→4)-D-Glcp;
β-D-Galp-(1→4)-β-D-Galp-(1→4)-β-D-Galp-(1→2)-D-Glcp;
β-D-Galp-(1→4)-β-D-Galp-(1→4)-β-D-Galp-(1→3)-D-Glcp;
β-D-Galp-(1→6)-β-D-Galp-(1→3)-D-Glcp;
β-D-Galp-(1→6)-β-D-Galp-(1→4)-β-D-Galp-(1→3)-D-Glcp;
β-D-Galp-(1→3)-β-D-Galp-(1→6)-D-Glcp;
β-D-Galp-(1→3)-β-D-Galp-(1→3)-D-Glcp;
β-D-Galp-(1→3)-β-D-Galp-(1→2)-D-Glcp;

β-D-Galp-(1→3)-β-D-Galp-(1→3)-β-D-Galp-(1→4)-D-Glcp;
β-D-Galp-(1→3)-β-D-Galp-(1→3)-β-D-Galp-(1→3)-D-Glcp;
β-D-Galp-(1→3)-β-D-Galp-(1→3)-β-D-Galp-(1→2)-D-Glcp;
β-D-Galp-(1→3)-β-D-Galp-(1→6)-β-D-Galp-(1→4)-D-Glcp; and
β-D-Galp-(1→3)-[β-DGalp-(1→6)-]β-D-Galp-(1→4)-D-Glcp.

24. The GOS composition of claim 8, wherein the GOS composition is essentially free of one or more of:
β-D-Galp-(1→4)-[β-D-Galp-(1→6)-]D-Glcp;
β-D-Galp-(1→4)-D-Galp;
β-D-Galp-(1→2)-[β-D-Galp-(1→4)-]D-Glcp;
β-D-Galp-(1→2)-[β-D-Galp-(1→6)-]D-Glcp;
β-D-Galp-(1→3)-[β-D-Galp-(1→6)-]D-Glcp;
β-D-Galp-(1→4)-β-D-Galp-(1→2)-D-Glcp;
β-D-Galp-(1→4)-β-D-Galp-(1→3)-D-Glcp;
β-D-Galp-(1→4)-[β-D-Galp-(1→4)-β-D-Galp-(1→6)-]D-Glcp;
β-D-Galp-(1→4)-β-D-Galp-(1→4)-[β-D-Galp-(1→6)-]D-Glcp;
β-D-Galp-(1→4)-β-D-Galp-(1→4)-[β-D-Galp-(1→2)-]D-Glcp;
β-D-Galp-(1→4)-β-D-Galp-(1→2)-[β-D-Galp-(1→4)-]D-Glcp;
β-D-Galp-(1→4)-β-D-Galp-(1→2)-[β-D-Galp-(1→6)-]D-Glcp;
β-D-Galp-(1→4)-β-D-Galp-(1→6)-[β-D-Galp-(1→2)-]D-Glcp;
β-D-Galp-(1→4)-β-D-Galp-(1→4)β-D-Galp-(1→6)-D-Glcp;
β-D-Galp-(1→4)-β-D-Galp-(1→4)β-D-Galp-(1→4)-D-Glcp;
β-D-Galp-(1→4)-β-D-Galp-(1→4)β-D-Galp-(1→2)-D-Glcp;
β-D-Galp-(1→4)-β-D-Galp-(1→4)β-D-Galp-(1→3)-D-Glcp;
β-D-Galp-(1→6)-β-D-Galp-(1→3)-D-Glcp;
β-D-Galp-(1→6)-β-D-Galp-(1→4)-β-D-Galp-(1→3)-D-Glcp;
β-D-Galp-(1→3)-β-D-Galp-(1→6)-D-Glcp;
β-D-Galp-(1→3)-β-D-Galp-(1→3)-D-Glcp;
β-D-Galp-(1→3)-β-D-Galp-(1→2)-D-Glcp;
β-D-Galp-(1→3)-β-D-Galp-(1→3)-β-D-Galp-(1→4)-D-Glcp;
β-D-Galp-(1→3)-β-D-Galp-(1→3)-β-D-Galp-(1→3)-D-Glcp;
β-D-Galp-(1→3)-β-D-Galp-(1→3)-β-D-Galp-(1→2)-D-Glcp;
β-D-Galp-(1→3)-β-D-Galp-(1→6)-β-D-Galp-(1→4)-D-Glcp; and
β-D-Galp-(1→3)-[β-DGalp-(1→6)-]β-D-Galp-(1→4)-D-Glcp.

25. The GOS composition of claim 9, wherein the GOS composition is essentially free of one or more of:
β-D-Galp-(1→4)-[β-D-Galp-(1→6)-]D-Glcp;
β-D-Galp-(1→4)-D-Galp;
β-D-Galp-(1→2)-[β-D-Galp-(1→4)-]D-Glcp;
β-D-Galp-(1→2)-[β-D-Galp-(1→6)-]D-Glcp;
β-D-Galp-(1→3)-[β-D-Galp-(1→6)-]D-Glcp;
β-D-Galp-(1→4)-β-D-Galp-(1→2)-D-Glcp;
β-D-Galp-(1→4)-β-D-Galp-(1→3)-D-Glcp;
β-D-Galp-(1→4)-[β-D-Galp-(1→4)-β-D-Galp-(1→6)-]D-Glcp;
β-D-Galp-(1→4)-β-D-Galp-(1→4)-[β-D-Galp-(1→6)-]D-Glcp;
β-D-Galp-(1→4)-β-D-Galp-(1→4)-[β-D-Galp-(1→2)-]D-Glcp;
β-D-Galp-(1→4)-β-D-Galp-(1→2)-[β-D-Galp-(1→4)-]D-Glcp;
β-D-Galp-(1→4)-β-D-Galp-(1→2)-[β-D-Galp-(1→6)-]D-Glcp;
β-D-Galp-(1→4)-β-D-Galp-(1→6)-[β-D-Galp-(1→2)-]D-Glcp;
β-D-Galp-(1→4)-β-D-Galp-(1→4)-β-D-Galp-(1→6)-D-Glcp;
β-D-Galp-(1→4)-β-D-Galp-(1→4)-β-D-Galp-(1→4)-D-Glcp;
β-D-Galp-(1→4)-β-D-Galp-(1→4)-β-D-Galp-(1→2)-D-Glcp;
β-D-Galp-(1→4)-β-D-Galp-(1→4)-β-D-Galp-(1→3)-D-Glcp;
β-D-Galp-(1→6)-β-D-Galp-(1→3)-D-Glcp;
β-D-Galp-(1→6)-β-D-Galp-(1→4)-β-D-Galp-(1→3)-D-Glcp;
β-D-Galp-(1→3)-β-D-Galp-(1→6)-D-Glcp;
β-D-Galp-(1→3)-β-D-Galp-(1→3)-D-Glcp;
β-D-Galp-(1→3)-β-D-Galp-(1→2)-D-Glcp;
β-D-Galp-(1→3)-β-D-Galp-(1→3)-β-D-Galp-(1→4)-D-Glcp;
β-D-Galp-(1→3)-β-D-Galp-(1→3)-β-D-Galp-(1→3)-D-Glcp;
β-D-Galp-(1→3)-β-D-Galp-(1→3)-β-D-Galp-(1→2)-D-Glcp;
β-D-Galp-(1→3)-β-D-Galp-(1→6)-β-D-Galp-(1→4)-D-Glcp; and
β-D-Galp-(1→3)-[β-DGalp-(1→6)-]β-D-Galp-(1→4)-D-Glcp.

26. The GOS composition of claim 10, wherein the GOS composition is essentially free of one or more of:
β-D-Galp-(1→4)-[β-D-Galp-(1→6)-]D-Glcp;
β-D-Galp-(1→4)-D-Galp;
β-D-Galp-(1→2)-[β-D-Galp-(1→4)-]D-Glcp;
β-D-Galp-(1→2)-[β-D-Galp-(1→6)-]D-Glcp;
β-D-Galp-(1→3)-[β-D-Galp-(1→6)-]D-Glcp;
β-D-Galp-(1→4)-β-D-Galp-(1→2)-D-Glcp;
β-D-Galp-(1→4)-β-D-Galp-(1→3)-D-Glcp;
β-D-Galp-(1→4)-[β-D-Galp-(1→4)β-D-Galp-(1→6)-]D-Glcp;
β-D-Galp-(1→4)-β-D-Galp-(1→4)-[β-D-Galp-(1→6)-]D-Glcp;
β-D-Galp-(1→4)-β-D-Galp-(1→4)-[β-D-Galp-(1→2)-]D-Glcp;
β-D-Galp-(1→4)-β-D-Galp-(1→2)-[β-D-Galp-(1→4)-]D-Glcp;
β-D-Galp-(1→4)-β-D-Galp-(1→2)-[β-D-Galp-(1→6)-]D-Glcp;
β-D-Galp-(1→4)-β-D-Galp-(1→6)-[β-D-Galp-(1→2)-]D-Glcp;
β-D-Galp-(1→4)-β-D-Galp-(1→4)-β-D-Galp-(1→6)-D-Glcp;
β-D-Galp-(1→4)-β-D-Galp-(1→4)-β-D-Galp-(1→4)-D-Glcp;
β-D-Galp-(1→4)-β-D-Galp-(1→4)-β-D-Galp-(1→2)-D-Glcp;
β-D-Galp-(1→4)-β-D-Galp-(1→4)-β-D-Galp-(1→3)-D-Glcp;
β-D-Galp-(1→6)-β-D-Galp-(1→3)-D-Glcp;
β-D-Galp-(1→6)-β-D-Galp-(1→4)-β-D-Galp-(1→3)-D-Glcp;
β-D-Galp-(1→3)-β-D-Galp-(1→6)-D-Glcp;

β-D-Galp-(1→3)-β-D-Galp-(1→3)-D-Glcp;
β-D-Galp-(1→3)-β-D-Galp-(1→2)-D-Glcp;
β-D-Galp-(1→3)-β-D-Galp-(1→3)-β-D-Galp-(1→4)-D-Glcp;
β-D-Galp-(1→3)-β-D-Galp-(1→3)-β-D-Galp-(1→3)-D-Glcp;
β-D-Galp-(1→3)-β-D-Galp-(1→3)-β-D-Galp-(1→2)-D-Glcp;
β-D-Galp-(1→3)-β-D-Galp-(1→6)-β-D-Galp-(1→4)-D-Glcp; and
β-D-Galp-(1→3)-[β-DGalp-(1→6)-]β-D-Galp-(1→4)-D-Glcp.

27. The GOS composition of claim 12, wherein the GOS composition is essentially free of one or more of:
β-D-Galp-(1→4)-[β-D-Galp-(1→6)-]D-Glcp;
β-D-Galp-(1→4)-D-Galp;
β-D-Galp-(1→2)-[β-D-Galp-(1→4)-]D-Glcp;
β-D-Galp-(1→2)-[β-D-Galp-(1→6)-]D-Glcp;
β-D-Galp-(1→3)-[β-D-Galp-(1→6)-]D-Glcp;
β-D-Galp-(1→4)-β-D-Galp-(1→2)-D-Glcp;
β-D-Galp-(1→4)-β-D-Galp-(1→3)-D-Glcp;
β-D-Galp-(1→4)-[β-D-Galp-(1→4)-β-D-Galp-(1→6)-]D-Glcp;
β-D-Galp-(1→4)-β-D-Galp-(1→4)-[β-D-Galp-(1→6)-]D-Glcp;
β-D-Galp-(1→4)-β-D-Galp-(1→4)-[β-D-Galp-(1→2)-]D-Glcp;
β-D-Galp-(1→4)-β-D-Galp-(1→2)-[β-D-Galp-(1→4)-]D-Glcp;
β-D-Galp-(1→4)-β-D-Galp-(1→2)-[β-D-Galp-(1→6)-]D-Glcp;
β-D-Galp-(1→4)-β-D-Galp-(1→6)-[β-D-Galp-(1→2)-]D-Glcp;
β-D-Galp-(1→4)-β-D-Galp-(1→4)-β-D-Galp-(1→6)-D-Glcp;
β-D-Galp-(1→4)-β-D-Galp-(1→4)-β-D-Galp-(1→4)-D-Glcp;
β-D-Galp-(1→4)-β-D-Galp-(1→4)-β-D-Galp-(1→2)-D-Glcp;
β-D-Galp-(1→4)-β-D-Galp-(1→4)-β-D-Galp-(1→3)-D-Glcp;
β-D-Galp-(1→6)-β-D-Galp-(1→3)-D-Glcp;
β-D-Galp-(1→6)-β-D-Galp-(1→4)-β-D-Galp-(1→3)-D-Glcp;
β-D-Galp-(1→3)-β-D-Galp-(1→6)-D-Glcp;
β-D-Galp-(1→3)-β-D-Galp-(1→3)-D-Glcp;
β-D-Galp-(1→3)-β-D-Galp-(1→2)-D-Glcp;
β-D-Galp-(1→3)-β-D-Galp-(1→3)-β-D-Galp-(1→4)-D-Glcp;
β-D-Galp-(1→3)-β-D-Galp-(1→3)-β-D-Galp-(1→3)-D-Glcp;
β-D-Galp-(1→3)-β-D-Galp-(1→3)-β-D-Galp-(1→2)-D-Glcp;
β-D-Galp-(1→3)-β-D-Galp-(1→6)-β-D-Galp-(1→4)-D-Glcp; and
β-D-Galp-(1→3)-[β-DGalp-(1→6)-]β-D-Galp-(1→4)-D-Glcp.

28. The GOS composition of claim 14, wherein the GOS composition is essentially free of one or more of:
β-D-Galp-(1→4)-[β-D-Galp-(1→6)-]D-Glcp;
β-D-Galp-(1→4)-D-Galp;
β-D-Galp-(1→2)-[β-D-Galp-(1→4)-]D-Glcp;
β-D-Galp-(1→2)-[β-D-Galp-(1→6)-]D-Glcp;
β-D-Galp-(1→3)-[β-D-Galp-(1→6)-]D-Glcp;
β-D-Galp-(1→4)-β-D-Galp-(1→2)-D-Glcp;
β-D-Galp-(1→4)-β-D-Galp-(1→3)-D-Glcp;
β-D-Galp-(1→4)-[β-D-Galp-(1→4)-β-D-Galp-(1→6)-]D-Glcp;
β-D-Galp-(1→4)-β-D-Galp-(1→4)-[β-D-Galp-(1→6)-]D-Glcp;
β-D-Galp-(1→4)-β-D-Galp-(1→4)-[β-D-Galp-(1→2)-]D-Glcp;
β-D-Galp-(1→4)-β-D-Galp-(1→2)-[β-D-Galp-(1→4)-]D-Glcp;
β-D-Galp-(1→4)-β-D-Galp-(1→2)-[β-D-Galp-(1→6)-]D-Glcp;
β-D-Galp-(1→4)-β-D-Galp-(1→6)-[β-D-Galp-(1→2)-]D-Glcp;
β-D-Galp-(1→4)-β-D-Galp-(1→4)-β-D-Galp-(1→6)-D-Glcp;
β-D-Galp-(1→4)-β-D-Galp-(1→4)-β-D-Galp-(1→4)-D-Glcp;
β-D-Galp-(1→4)-β-D-Galp-(1→4)-β-D-Galp-(1→2)-D-Glcp;
β-D-Galp-(1→4)-β-D-Galp-(1→4)-β-D-Galp-(1→3)-D-Glcp;
β-D-Galp-(1→6)-β-D-Galp-(1→3)-D-Glcp;
β-D-Galp-(1→6)-β-D-Galp-(1→4)-β-D-Galp-(1→3)-D-Glcp;
β-D-Galp-(1→3)-β-D-Galp-(1→6)-D-Glcp;
β-D-Galp-(1→3)-β-D-Galp-(1→3)-D-Glcp;
β-D-Galp-(1→3)-β-D-Galp-(1→2)-D-Glcp;
β-D-Galp-(1→3)-β-D-Galp-(1→3)-β-D-Galp-(1→4)-D-Glcp;
β-D-Galp-(1→3)-β-D-Galp-(1→3)-β-D-Galp-(1→3)-D-Glcp;
β-D-Galp-(1→3)-β-D-Galp-(1→3)-β-D-Galp-(1→2)-D-Glcp;
β-D-Galp-(1→3)-β-D-Galp-(1→6)-β-D-Galp-(1→4)-D-Glcp; and
β-D-Galp-(1→3)-[β-DGalp-(1→6)-]β-D-Galp-(1→4)-D-Glcp.

29. The food item of claim 3, wherein the food item is animal feed.

30. A dietary supplement comprising a galactooligosaccharide (GOS) composition as defined in claim 5.

* * * * *

UNITED STATES PATENT AND TRADEMARK OFFICE
CERTIFICATE OF CORRECTION

PATENT NO. : 10,337,042 B2
APPLICATION NO. : 15/923957
DATED : July 2, 2019
INVENTOR(S) : Stephen Tomiuk Page 1 of 1

It is certified that error appears in the above-identified patent and that said Letters Patent is hereby corrected as shown below:

In the Claims

Lines 33-40 of Claim 24 should appear as follows:
β-D-Galp-(1→4)-β-D-Galp-(1→4)-β-D-Galp-(1→6)-D-Glcp;
β-D-Galp-(1→4)-β-D-Galp-(1→4)-β-D-Galp-(1→4)-D-Glcp;
β-D-Galp-(1→4)-β-D-Galp-(1→4)-β-D-Galp-(1→2)-D-Glcp;
β-D-Galp-(1→4)-β-D-Galp-(1→4)-β-D-Galp-(1→3)-D-Glcp;

Signed and Sealed this
Nineteenth Day of November, 2019

Andrei Iancu
*Director of the United States Patent and Trademark Office*